United States Patent [19]

Janssens et al.

[11] Patent Number: 5,025,014

[45] Date of Patent: Jun. 18, 1991

[54] BICYCLIC HETEROCYCLYL CONTAINING N-(BICYCLIC HETEROCYCLYL)-4-PIPERIDINAMINES AS PHARMACEUTICALS

[75] Inventors: Frans E. Janssens, Bonheiden; Joseph L. G. Torremans, Beerse; Jozef F. Hens, Nijlen; Theophilus T. J. M. Van Offenwert, Vosselaar, all of Belgium

[73] Assignee: Janssen Pharmaceutica N.V., Beerse, Belgium

[21] Appl. No.: 447,312

[22] Filed: Dec. 7, 1989

Related U.S. Application Data

[60] Division of Ser. No. 56,200, Jun. 1, 1987, Pat. No. 4,888,426, which is a division of Ser. No. 660,608, Oct. 12, 1987, Pat. No. 4,695,569, which is a continuation-in-part of Ser. No. 556,742, Nov. 30, 1983, abandoned.

[51] Int. Cl.$^5$ .................. A61K 31/505; A61K 31/52; C07D 487/04; C07D 473/04
[52] U.S. Cl. .................. 514/258; 514/259; 514/265; 544/268; 544/278; 544/284
[58] Field of Search .................. 544/268, 278, 284; 514/259, 265, 258

[56] References Cited

U.S. PATENT DOCUMENTS 4,219,559  8/1980  Janssens et al. .................. 424/267

Primary Examiner—Bernard I. Dentz
Attorney, Agent, or Firm—Charles J. Metz

[57] ABSTRACT

Bicyclic heterocyclyl containing N-(bicyclic heterocyclyl)-4-piperidinamines having antihistaminic and serontonin-antagonistic properties which compounds are useful agents in the treatment of allergic diseases.

18 Claims, No Drawings

BICYCLIC HETEROCYCLYL CONTAINING N-(BICYCLIC HETEROCYCLYL)-4-PIPERIDINAMINES AS PHARMACEUTICALS

CROSS-REFERENCE TO RELATED APPLICATIONS

This application is a divisional of application Ser. No. 56,200 filed Jun. 1, 1987 now U.S. Pat. No. 4,888,426, which was a divisional of application Ser. No. 660,608, filed Oct. 12, 1987, now U.S. Pat. No. 4,695,569, which was a continuation-in-part of application Ser. No. 556,742, filed Nov. 30, 1983, now abandoned.

BACKGROUND OF THE INVENTION

In U.S. Pat. No. 4,219,559 there are described a number of N-heterocyclyl-4-piperidinamines having the formula

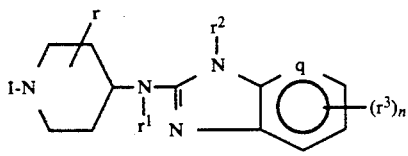

which compounds are useful as antihistaminic agents.

The compounds of the present invention differ from the prior art compounds essentially by the nature of the 1-piperidinyl substituent and by the fact that the compounds of the present invention are not only potent histamine-antagonists but also potent serotonin-antagonists.

DESCRIPTION OF THE PREFERRED EMBODIMENTS

This invention is concerned with novel N-heterocyclyl-4-piperidinamines which may structurally be represented by the formula

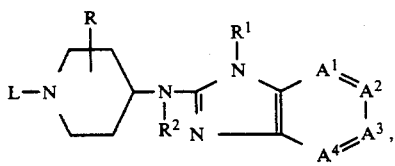

the pharmaceutically acceptable acid addition salts and the possible stereochemically isomeric forms thereof, wherein:

$A^1=A^2-A^3=A^4$ is a bivalent radical having the formula

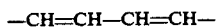  —CH=CH—CH=CH— (a),

  —N=CH—CH=CH— (b),

  —CH=N—CH=CH— (c),

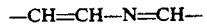  —CH=CH—N=CH— (d), or

  —CH=CH—CH=N— (e), wherein one or two hydrogen atoms in said radicals (a)–(e) may, each independently from each other, be replaced by halo, lower alkyl, lower alkyloxy, trifluoromethyl or hydroxy;

R is a member selected from the group consisting of hydrogen and lower alkyl;

$R^1$ is a member selected from the group consisting of hydrogen, alkyl, cycloalkyl, $Ar^1$ and lower alkyl substituted with one or two $Ar^1$ radicals;

$R^2$ is a member selected from the group consisting of hydrogen, lower alkyl, cycloalkyl, (lower alkyl)—CO—, lower alkyl—O—(CO)— and $Ar^2$-lower alkyl;

L is a member selected from the group consisting of a radical of formula

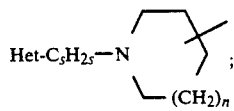  (f)

a radical of formula

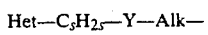  Het—$C_sH_{2s}$—Y—Alk— (g);

and a radical of formula

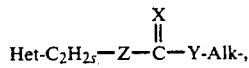  (h)

wherein n is 0 or the integer 1 or 2;
s is 0 or an integer from 1 to 6 inclusive;
Alk is lower alkanediyl;
Y is O, S, $NR^3$ or a direct bond;
X is O, S, CH-$NO_2$ or $NR^4$;
Z is O, S, $NR^5$ or a direct bond; and
Het is an optionally substituted five- or six-membered heterocyclic ring containing at least one nitrogen atom and being condensed with an optionally substituted five- or six-membered ring, provided that:
  (i) when Het is connected to $C_sH_{2s}$ on a carbon atom then said five- or six-membered ring is not condensed with an optionally substituted benzene ring;
  (ii) when L is a radical either of formula (f), or of formula (g) wherein Y is other than a direct bond, or of formula (h) wherein Z is other than a direct bond, wherein in said radicals (f), (g) or (h) Het is connected to $C_sH_{2s}$ on a nitrogen atom then s is not 0;
  (iii) when $A^1=A^2-A^3=A^4$ is a radical of formula (a) or (b) and L is a radical of formula (g) wherein s is 0 and Y is a direct bond then Het is other than a 2,3-dihydro-2-oxo-1H-benzimidazol-1-yl or a 2,3-dihydro-3-oxobenzoxazin-4-yl radical;

said $R^3$ being hydrogen, lower alkyl, ($Ar^2$)lower alkyl, 2-lower alkyloxy-1,2-dioxoethyl or a radical of formula —C(=X)—$R^6$, $R^6$ being hydrogen, lower alkyl, $Ar^2$, $Ar^2$-lower alkyl, lower alkyloxy, $Ar^2$-lower alkyloxy, mono- or di(lower alkyl)amino, $Ar^2$-amino, $Ar^2$-lower alkylamino or $Ar^2$-lower alkyl(lower alkyl)amino;

said $R^4$ being hydrogen, lower alkyl, cyano, nitro, $Ar^2$-sulfonyl, lower alkylsulfonyl, lower alkylcarbonyl or $Ar^2$-carbonyl; and said $R^5$ being hydrogen or lower alkyl;

wherein Ar¹ is a member selected from the group consisting of phenyl, being optionally substituted with up to three substituents each independently selected from the group consisting of halo, hydroxy, nitro, cyano, trifluoromethyl, lower alkyl, lower alkyloxy, lower alkylthio, mercapto, amino, mono- and di(-lower alkyl)amino, carboxyl, lower alkyloxycarbonyl and lower alkyl—CO—; thienyl; halothienyl; furanyl; lower alkyl substituted furanyl; pyridinyl; pyrazinyl; thiazolyl and imidazolyl optionally substituted by lower alkyl; and wherein Ar² is a member selected from the group consisting of phenyl being optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and (lower alkyl)—CO.

As used in the foregoing definitions the term halo is generic to fluoro, chloro, bromo and iodo; the term "lower alkyl" is meant to include straight and branch chained saturated hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like; "alkyl" is meant to include lower alkyl radicals, as defined hereinabove, and the higher homologs thereof having from 7 to 10 carbon atoms; the term "cycloalkyl" is generic to cyclopropyl, cyclobutyl, cyclopentyl and cyclohexyl; and "lower alkanediyl" is meant to include bivalent straight or branch chained alkanediyl radicals having from 1 to 6 carbon atoms.

It is evident that in the compounds of formula (I) the bicyclic condensed ring system may be unsaturated or partly or completely saturated.

The compounds of formula (I) wherein Het is a heterocycle which is substituted with a hydroxy, mercapto or amino radical may contain in their structure a keto-enol tautomeric system or a vinylog system thereof and consequently these compounds may be present in their keto form as well as their enol form.

Preferred compounds within the invention are those wherein Het is a member of the group consisting of

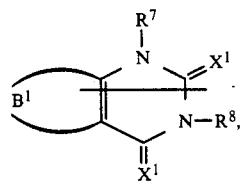  (i-1)

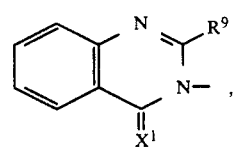  (i-2)

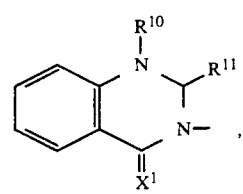  (i-3)

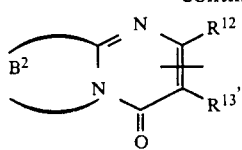  (i-4)

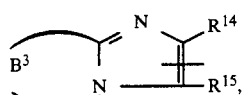  (i-5)

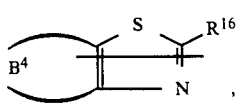  (i-6)

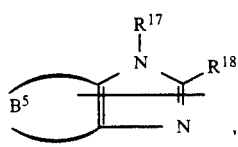  (i-7)

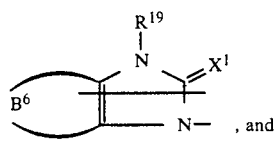  (i-8)

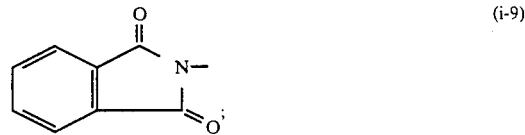  (i-9)

wherein
each $X^1$ is independently O or S;
$R^7$, $R^8$, $R^{10}$, $R^{17}$ and $R^{19}$ are each independently hydrogen, lower alkyl, Ar²-lower alkyl, hydroxylower alkyl or lower alkyloxycarbonyl;
$R^9$, $R^{11}$, $R^{12}$, $R^{13}$, $R^{14}$, $R^{15}$, $R^{16}$ and $R^{18}$ are each independently hydrogen, lower alkyl, hydroxy, mercapto, lower alkyloxy, lower alkylthio, halo and (lower alkyloxycarbonyl)lower alkyl;
$B^1$ is —CH=CH—CH=CH—, —S—CH=CH— or —N=CH—NH—;
$B^2$ is —CH=CH—CH=CH—, —S—(CH₂)₂, —S—(CH₂)₃, or —(CH₂)₄;
$B^3$ is —CH=CH—CH=CH—, —CH=N—CH=CH—, —CH₂—NH—(CH₂)₂—, —S—CH=CH— or —N=CH—CH=CH—;
$B^4$ is —CH₂—NH—(CH₂)₂—, —N=CH—CH=CH— or —N=CH—N=CH—;
$B^5$ is —N=CH—CH=CH—, —CH=CH—N=CH— or —CH=N—CH=N—;
$B^6$ is —CH=CH—CH=CH— or —CH=N—CH=N—;
wherein one or two hydrogen atoms in said radicals $B^1$, $B^2$, $B^3$, $B^4$, $B^5$ or $B^6$ or in the benzene part of the radicals of formula (i-2), (i-3) or (i-9) may be replaced by lower alkyl, lower alkylthio, lower alkyloxy or halo where said hydrogen atom is bonded on a carbon atom, or by lower alkyl, lower alkyloxycarbonyl, Ar²-lower alkyl, where said hydrogen is bonded on a nitrogen atom.

It is clear that $R^7$, $R^8$, $R^{12}$, $R^{13}$, $R^{14}$, $R^{15}$, $R^{16}$, $R^{17}$ or $R^{18}$ is absent where the radical of formula (i-1), respectively (i-4), (i-5), (i-6) and (i-7) is connected to $C_sH_{2s}$ on the atom bearing $R^7$, $R^8$, $R^{12}$, $R^{13}$, $R^{14}$, $R^{15}$, $R^{16}$, $R^{17}$ or $R^{18}$.

Particularly preferred compounds are those wherein L is a radical (g) or (h) wherein Het is as described hereinabove for the preferred compounds.

In order to simplify the structural representations of the compounds of formula (I) and of certain precursors and intermediates thereof the

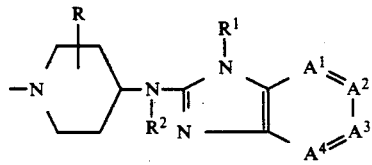

radical will hereafter be represented by the symbol D.

The compounds of formula (I) can generally be prepared by reacting an intermediate of formula (II) with a piperidine of formula (III) following art-known alkylating procedures.

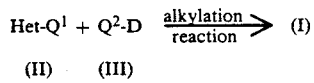

In (II) and (III) $Q^1$ and $Q^2$ are selected so that in combination with Het a bivalent radical of formula (f), (g) or (h) is formed during the alkylation reaction, said (f), (g) and (h) having the previously described meaning. For example, the compounds of formula (I) can generally be prepared by N-alkylating a piperidine of formula (III) wherein $Q^2$ is hydrogen, said piperidine being represented by the formula (III-a), with a reagent of formula (II) having the general formula L-W, (II-a).

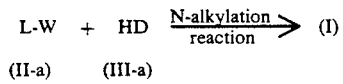

In (II-a) W represents an appropriate reactive leaving group such as, for example, halo, e.g., chloro, bromo or iodo, or a sulfonyloxy group, e.g. methylsulfonyloxy or 4-methylphenylsulfonyloxy.

Additionally, the compounds of formula (I) wherein L is a radical of formula (f), a radical of formula (g) wherein Y is other than a direct bond, $Y^1$, or a radical of formula (h) wherein Z is other than a direct bond, $Z^1$, said compounds being represented by the formulae (I-a-1), respectively (I-a-2) and (I-a-3), can be prepared by alkylating an intermediate of formula (III-b) with a reagent of formula (II-b).

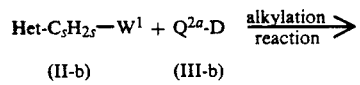

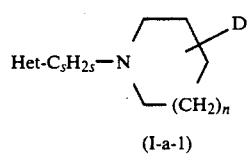

(I-a-1)

In (III-b) $Q^{2a}$ is a radical of formula

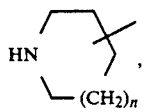

respectively a radical of formula $HY^1$-Alk- or

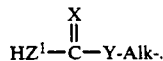

In (II-b) $W^1$ has the previously defined meaning of W and, where s is 0, it may also represent a lower alkyloxy, lower alkylthio or lower alkylsulfonyl group.

The compounds of formula (I-a-2) may also be prepared by alkylating a piperidine of formula (III) wherein $Q^2$ is a radical of formula —Alk—W, said piperidine being represented by the formula (III-c), with a reagent of formula (II) wherein $Q^1$ is a radical of formula —$C_sH_{2s}$—$Y^1H$, said reagent being represented by the formula (II-c).

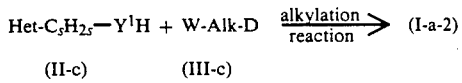

The compounds of formula (I) wherein L is a radical of formula Het—$C_sH_{2s}$—Z—C(=X)—$Y^1$—Alk, said compounds being represented by the formula (I-a-4), may also be prepared by N-alkylating a piperidine of formula (III-c) with a reagent of formula (II) wherein $Q^2$ is a radical of formula —$C_sH_{2s}$—Z—C(=X)—$Y^1H$, said reagent being represented by the formula (II-d).

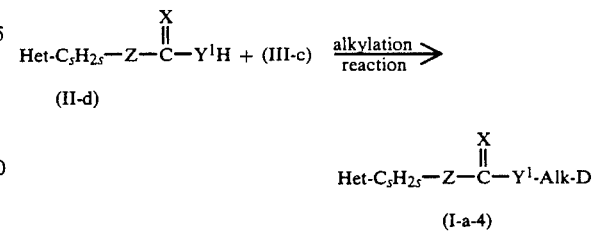

The alkylation reactions are conveniently conducted in an inert organic solvent such as, for example, an aromatic hydrocarbon, e.g., benzene, methylbenzene, dimethylbenzene, and the like; a lower alkanol, e.g., methanol, ethanol, 1-butanol and the like; a ketone, e.g., 2-propanone, 4-methyl-2-pentanone and the like; an ether, e.g., 1,4-dioxane, 1,1'-oxybisethane, tetrahydrofuran and the like; N,N-dimethylformamide (DMF); N,N-dimethylacetamide (DMA); nitrobenzene; 1-methyl-2-pyrrolidinone; and the like. The addition of an appropriate base such as, for example, an alkali metal carbonate or hydrogen carbonate, sodium hydride or an organic base such as, for example, N,N-diethylethanamine or N-(1-methylethyl)-2-propanamine may be utilized to pick up the acid which is liberated during the course of the reaction. In some circumstances the addition of an iodide salt, preferably an alkali metal iodide, is appropriate. Somewhat elevated temperatures may enhance the rate of the reaction.

The compounds of formula (I) can also be prepared by the cyclodesulfurization reaction of an appropriate thiourea derivative of the formula

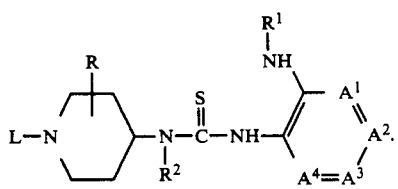

Said cyclodesulfurization reaction may be carried out by the reaction of (IV) with an appropriate alkyl halide, preferably iodomethane in an appropriate reaction-inert organic solvent, e.g., a lower alkanol such as methanol, ethanol, 2-propanol and the like. Otherwise, the cyclodesulfurization reaction may be carried out by the reaction of (IV) with an appropriate metal oxide or salt in an appropriate solvent according to art-known procedures. For example, the compounds of formula (I) can easily be prepared by the reaction of (IV) with an appropriate Hg(II) or Pb(II) oxide or salt, such as, for example HgO, HgCl$_2$, Hg(OAc)$_2$, PbO or Pb(OAc)$_2$. In certain instances it may be appropriate to supplement the reaction mixture with a small amount of sulfur. Even so methanediimines, especially N,N'-methanetetraylbis[cyclohexanamine] may be used as cyclodesulfurizing agents.

The compounds of formula (I) wherein L is a radical of formula (h) wherein Z is $Z^1$, Y is NH and X is O or S, said X being represented by $X^1$ and said compounds by the formula (I-b-1), can generally be prepared by reacting an isocyanate or isothiocyanate of formula (V) with a reagent of formula (VI).

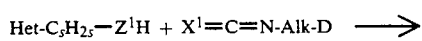

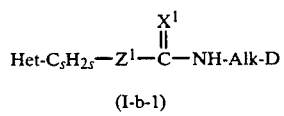

The compounds of formula (I) wherein L is a radical of formula (h) wherein Z is NH, Y is $Y^1$ and X is $X^1$, said compounds being represented by the formula (I-b-2), can be prepared by reacting an isocyanate or isothiocyanate of formula (VII) with a piperidine of formula (VIII).

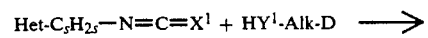

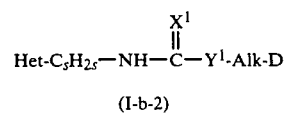

The reaction of (V) with (VI) and (VII) with (VIII) is generally conducted in a suitable reaction-inert solvent such as, for example, an ether, e.g. tetrahydrofuran and the like. Elevated temperatures may be suitable to enhance the rate of the reaction.

The compounds of formula (I) wherein L is a radical of formula (h) wherein Z is a direct bond and X is $X^1$, said compounds being represented by the formula (I-c), may be prepared by reacting a piperidine of formula (VIII) with a reagent of formula (IX).

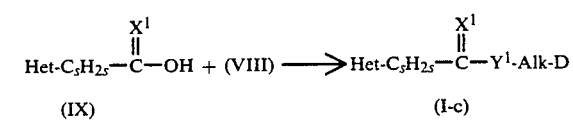

The reaction of (VIII) with (IX) may generally be conducted following art-known esterification- or amidation reaction procedures. For example, the carboxylic acid may be converted into a reactive derivative, e.g. an anhydride or a carboxylic acid halide, which subsequently, is reacted with (VIII); or by reacting (VIII) and (IX) with a suitable reagent capable of forming amides or esters, e.g. dicyclohexylcarbodiimide, 2-chloro-1-methylpyridinium iodide and the like. Said reactions are most conveniently conducted in a suitable solvent such as, for example, an ether, e.g. tetrahydrofuran, a halogenated hydrocarbon, e.g. dichloromethane, trichloromethane or a polar aprotic solvent, e.g. N,N-dimethylformamide. The addition of a base, e.g. N,N-diethylethanamine may be appropriate.

The compounds of formula (I) wherein L is a radical of formula (g) wherein Y is a direct bond and s is 0, said compounds being represented by the formula (I-d), may also be prepared by reacting an appropriate alkenylene of formula (X) with a piperidine of formula (III-a) by stirring and, if desired, heating the reactants together.

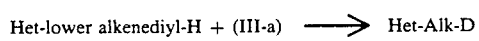

The compounds of formula (I) wherein L is a radical of formula (g), wherein Het is a radical of formula (i-5) wherein $R^{15}$ is hydrogen, s is 0, Y is a direct bond and —Alk— is —CH$_2$—, said compounds being represented by the formula (I-e) may conveniently be prepared by reacting an intermediate of formula H-D (III-a) with a reagent of formula (XI) in the presence of formaldehyde or a polymeric form thereof.

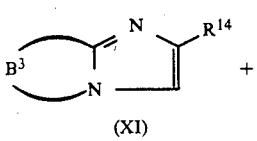

CH$_2$O or polymeric + (III-a) ⟶
form thereof

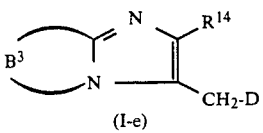

Said reaction may conveniently be conducted in a suitable solvent, e.g. water, acetic acid, propanoic acid or mixtures of such solvents. Elevated temperatures may be appropriate to enhance the reaction rate.

The compounds of formula (I) may also be prepared following procedures for preparing condensed bicyclic ringsystems which are known in the art or analogous procedures thereof. A number of such cyclization procedures will be described hereinafter.

The bivalent radical K used in the description of these cyclization reactions has the following meaning:

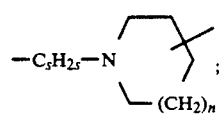  (j-1)

$-C_sH_{2s}-Y-Alk-$; or  (j-2)

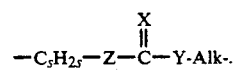  (j-3)

For example, where Het is a radical of formula (i-1) being connected to K by the nitrogen atom bearing $R^8$, said Het may be formed by condensing an intermediate (XII) with a $>C=X^1$ generating agent, e.g. urea, thiourea, 1,1'-carbonylbis[1H-imidazole], lower alkyl carbonohalidate, phosgene, thiophosgene, trichloromethyl carbonohalidate and the like.

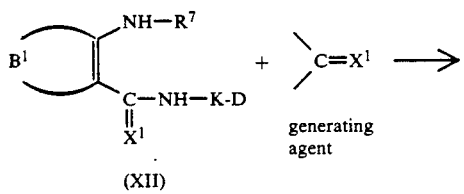

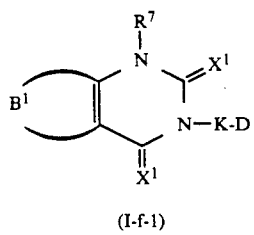

(I-f-1)

The compounds of formula (I-f-1) wherein $R^7$ is hydrogen may additionally be prepared by cyclizing an intermediate of formula

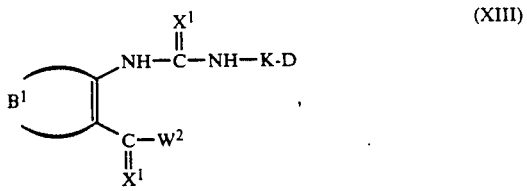

which may in situ be generated by reacting a reagent (XIV) with an amine (XV).

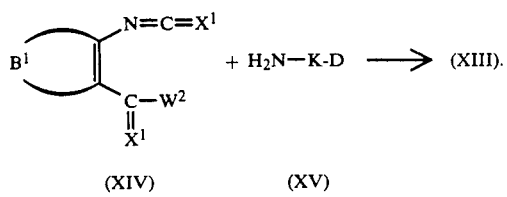

$W^2$ as used throughout the description of the final compounds and intermediates is an appropriate reactive leaving group, such as, for example, halo, e.g., chloro, bromo or iodo, a sulfonyloxy group, e.g. methylsulfonyloxy or 4-methylphenylsulfonyloxy, a lower alkyloxy, lower alkylthio, $Ar^2$-oxy or $Ar^2$-thio group. The reaction of (XII) with the $>C=X^1$ generating agent and the cyclization of (XIII) may conveniently be conducted in a suitable solvent such as, for example, an ether, e.g. 1,1-oxybisethane, tetrahydrofuran, an halogenated hydrocarbon, e.g. dichloromethane, trichloromethane, a hydrocarbon, e.g. benzene, methylbenzene, an alcohol, e.g. methanol, ethanol, a ketone, e.g. 2-propanone, 4-methyl-2-pentanone; N,N-dimethylformamide, N,N-dimethylacetamide, or mixtures of such solvents, optionally in the presence of an appropriate base such as, for example, N,N-diethylethanamine, an alkali or earth alkaline metal carbonate or hydrogen carbonate. In order to enhance the reaction rate, it may be suitable to heat the reaction mixture.

Further, where Het is a radical of formula (i-2), said Het may be generated by cyclizing an intermediate (XVI) with an acid (XVII) or a suitable functional derivative thereof, thus giving a compound of formula (I-f-2). Alternatively an intermediate (XVIII) may be condensed with an aromatic amino acid or -thioacid of formula (XIX), giving also a compound (I-f-2).

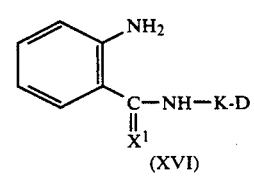  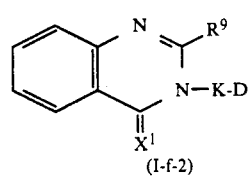

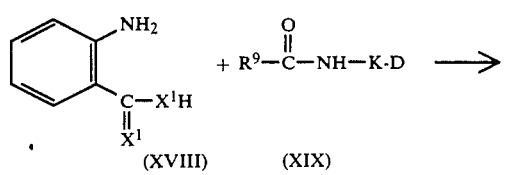

The reaction of (XVI) with (XVII) and of (XVIII) with (XIX) may be conducted in a suitable reaction-inert solvent, such as, for example, a hydrocarbon, e.g. benzene, methylbenzene, an alcohol, water. In some instances it may be appropriate to use higher temperatures in order to reduce the reaction time.

Where Het is a radical of formula (i-3), said Het may be formed by reacting the previously described intermediate (XVI) with an appropriate acetylene derivative (XX), thus giving a compound of formula (I-f-3).

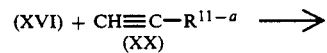

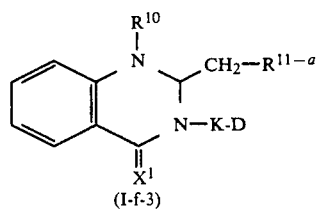

wherein $R^{11-a}$—CH$_2$— is a suitable substituent on said radical (i-3). The reaction of (XX) with (XVI) may be conducted in a suitable solvent such as, for example, an alcohol, e.g. methanol, ethanol. Elevated temperatures may also be appropriate to shorten the reaction time.

Additionally, where Het is a radical (i-5), said Het may be created by condensing a reagent (XXI) with an intermediate (XXII), thus giving a compound (I-f-4).

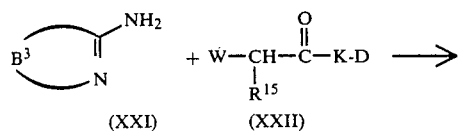

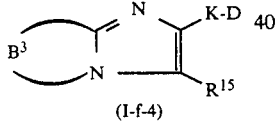

Further, where Het is a radical of formula (i-6), wherein Het is connected to K by the thiazole ring, said Het may be formed during the cyclization of a reagent (XXIII) with an intermediate (XXIV), thus giving a compound (I-f-5).

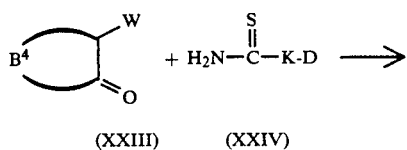

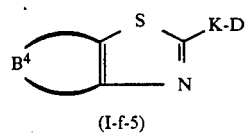

Where Het is a radical of formula (i-6) being connected to K by the B$^4$ containing ring and bearing a 2-mercaptosubstituent, said Het may be formed during the cyclization of an intermediate (XXV) with CS$_2$, thus giving a compound (I-f-6).

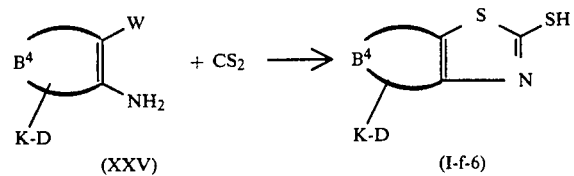

Where Het is a radical of formula (i-7) being connected to K either by the B$^5$ containing ring or by the imidazole ring, said Het is formed during the condensation reaction of a reagent (XXVI) with an intermediate (XXVII) respectively by the cyclodesulfurization reaction of an intermediate (XXVIII), thus giving a compound (I-f-7) respectively (I-f-8).

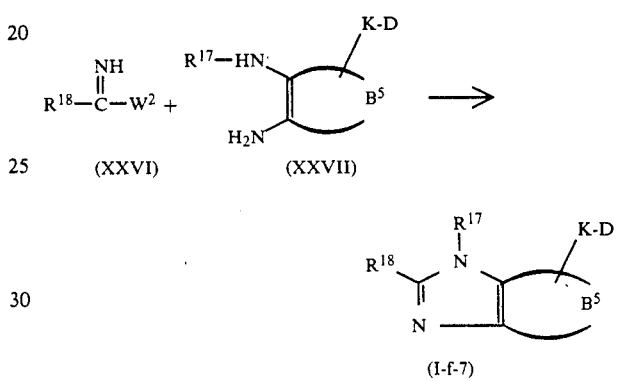

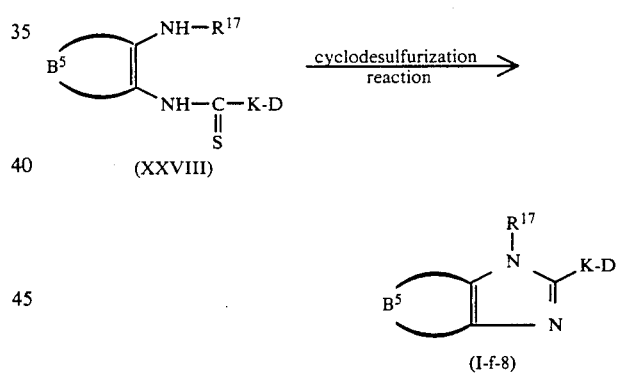

The reactions of (XXI) with (XXII), of (XXIII) with (XXIV), of (XXV) with CS$_2$ and (XXVI) with (XXVII) may conveniently conducted in a suitable reaction-inert solvent, such as for example one of the solvents given hereinabove for the preparation of (I-f-1) optionally in the presence of an appropriate base, e.g. one of the bases also described for the preparation of (I-f-1); higher temperature may be used to enhance the reaction rate. The cyclodesulfurization of (XXVIII) may be conducted following the same reaction circumstances as described hereinabove for the preparation of (I) starting from (IV).

Where Het is a radical (i-8), said Het may be formed furing the condensation of an intermediate (XXIX) with a >C=X$^1$ generating agent, following the same procedures as previously described for the preparation of (I-f-1) starting from (XII).

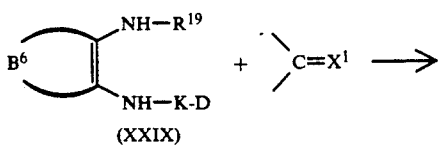

(XXIX)

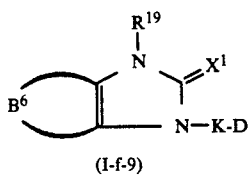

(I-f-9)

The compounds of formula (I) wherein L is a radical of formula (g), said compounds being represented by the formula (I-g), may also be generated by reducing an intermediate (XXX) with an appropriate complex metal hydride, e.g. lithium aluminium hydride, in a suitable solvent such as, for example, an ether, e.g. tetrahydrofuran, 1,1′-oxybisethane and the like.

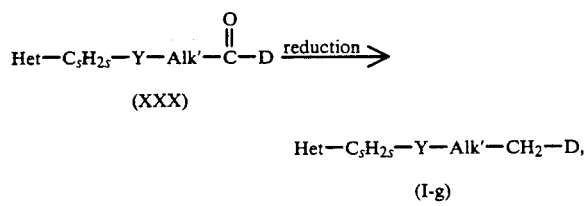

Alk′ having the previously defined meaning of Alk, provided that one methylene function is missing.

The compounds of formula (I) can also be converted into each other following art-known procedures of functional grouptransformation. Some examples will be cited hereinafter.

The compounds of formula (I) having a nitro substituent can be converted into their corresponding amines by stirring and, if desired, heating the starting nitrocompounds in a hydrogen-containing medium in the presence of a suitable amount of an appropriate catalyst such as, for example, platinum-on-charcoal, palladium-on-charcoal, Raney-nickel and the like catalysts. Suitable solvents are, for example, alcohols, e.g. methanol, ethanol and the like.

Halo atoms substituted on aryl groups may be replaced by hydrogen following art-known hydrogenolysis procedures, i.e. by stirring and, if desired, heating the starting compounds in a suitable solvent under hydrogen atmosphere in the presence of an appropriate catalyst, e.g. palladium-on-charcoal and the like catalysts. Said halo atoms may also be replaced by a lower alkyloxy or a lower alkylthio substituent by reacting the starting halo-compound with an appropriate alcohol or thioalcohol or, preferably, an alkali- or earth alkaline metal salt or an appropriate alcohol or thioalcohol in a suitable solvent.

The compounds of formula (I) wherein L is a radical (g) wherein Y is NH can be converted into a compound of formula (I) wherein L is a radical (g) wherein Y is N—CO(lower alkyl) or N—CO(Ar$^2$) by reacting the starting amine with an appropriate carboxylic acid or a derivative thereof such as, for example, an acid halide, an acid anhydride and the like.

The compounds of formula (I) wherein L is a radical (g) wherein Y is NH can be converted into a compound of formula (I) wherein L is a radical (g) wherein Y is N—CO(lower alkylamino), N—CO—NH—Ar$^2$, N—CS(lower alkylamino) or N—CS—NH—Ar$^2$ by reacting the starting amine with an appropriate isocyanate or isothiocyanate in a suitable solvent.

The compounds of formula (I) having an Het substituted with a thio (=S) radical may be converted into the corresponding oxo (=O) analogs by reacting the former compounds with a peroxide, e.g. hydrogen peroxide, in a suitable solvent.

Compounds of formula (I) containing an Het which is unsaturated may be converted into the corresponding compounds wherein Het is saturated or partly saturated following art-known reducing procedures.

In all of the foregoing and in the following preparations, the reaction products may be isolated from the reaction mixture and, if necessary, further purified according to methodologies generally known in the art.

The compounds of formula (I) have basic properties and, consequently, they may be converted to their therapeutically active non-toxic acid addition salt forms by treatment with appropriate acids, such as, for example, inorganic acids, such as hydrohalic acid, e.g. hydrochloric, hydrobromic and the like, and sulfuric acid, nitric acid, phosphoric acid and the like; or organic acids, such as, for example, acetic propanoic, hydroxyacetic, 2-hydroxypropanoic, ethanedioic, 2-oxopropanoic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

Some intermediates and starting materials in the foregoing preparations are known compounds which may be prepared according to art-known methodologies of preparing said or similar compounds and others are new. A number of such preparation methods will be described hereinafter in more detail.

The intermediates of formula (III-a) can conveniently be prepared starting from a thiourea derivative of formula

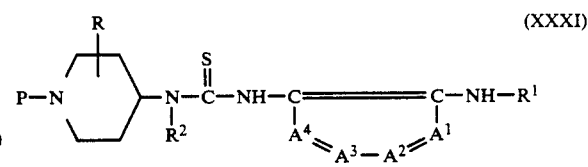

(XXXI)

wherein P is an appropriate protective group such as, for example, lower alkyloxycarbonyl, Ar$^2$—CH$_2$—O—CO—, Ar$^2$—CH$_2$— and the like, by a cyclodesulfurization reaction following the same procedure as described hereinabove for the preparation of (I) starting from (IV) and, subsequently eliminating the protective group P in the thus obtained intermediate of formula

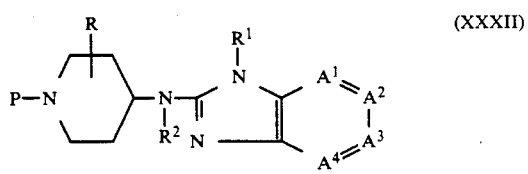

(XXXII)

The elimination of the protective group P in (XXXII) may generally be carried out following art-known procedures such as, for example, by hydrolysis in alkaline or acidic aqueous medium.

The intermediates of formula (III-b) and (III-c) may be derived from the corresponding intermediates of formula (III-a) by reacting the latter with a suitable reagent following art-known N-alkylating procedures.

For example, intermediates of formula (III-b) wherein $Q^{2a}$ represents a radical of formula $H_2N-CH_2-Alk'-$, (III-b-1), can also be prepared by reacting an intermediate of formula (III-a) with a nitrile of formula (XXXIII) following art-known N-alkylating procedures and subsequently converting the thus obtained nitrile (XXXIV) into the corresponding amine (III-b-1) following art-known nitrile to amine reducing procedures, e.g., by catalytically hydrogenating procedures and the like.

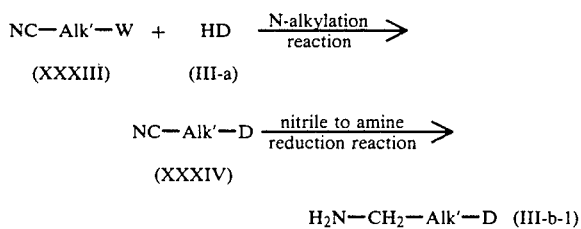

In (XXXIII), (XXXIV) and (III-b-1) Alk' has the same meaning as Alk provided that one methylene function is missing.

The intermediates of formula (III-b-1) may alternatively be prepared by reacting a reagent (XXXV) with (III-a) following art-known N-alkylating procedures and subsequently converting the thus formed intermediate (XXXVI) into the free amine following art-known deprotection procedures.

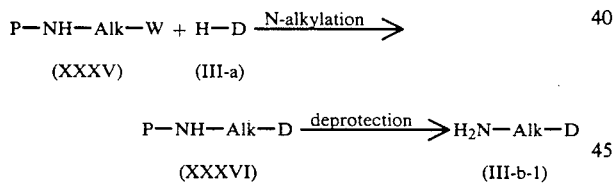

The intermediates of formula (III-b) wherein $Q^{2a}$ represents a radical of formula $HY^1-CH_2-CH_2-$, (III-b-2), may also be prepared by the reaction of (III-a) with a reagent of formula (XXXV) by stirring and, if desired, heating the reactants together in a suitable solvent.

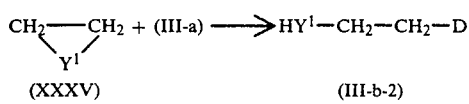

The intermediates of formula (III-b) wherein $Q^{2a}$ is a radical of formula $HY^1-Alk-$, (III-d), may be converted into an intermediate of formula (III-c) by converting the function $Y^1H$ into an appropriate leaving group, e.g., where $Y^1$ is O, by converting a hydroxy function into a chloro atom, with thionyl chloride, phosphoryl chloride and the like.

The intermediates of formula (III-b-1) may also be derived from an appropriate corresponding carbonyl-oxidated form by reacting said carbonyl-oxidated form with hydroxylamine and reducing the thus obtained oxime following art-known methods, e.g., catalytic hydrogenation and the like reducing methods.

During one of the reactions the intermediates wherein $R^1$ and/or $R^2$ and/or $R^3$ and/or $R^4$ is hydrogen may be converted into the corresponding intermediates wherein $R^1$ and/or $R^2$ and/or $R^3$ and/or $R^4$ is other than hydrogen following art-known N-alkylating, N-acylating or reductive N-alkylating procedures.

The intermediates of formula (XXXI) and the intermediates of formula (XXXI), wherein $R^2$ is hydrogen, said intermediates being represented by the formula (XXXI-a), may be prepared by reacting a piperidine of formula (XXXVI-a) or (XXXVI-b) with an aromatic reagent of formula (XXXVII-a) or (XXXVII-b).

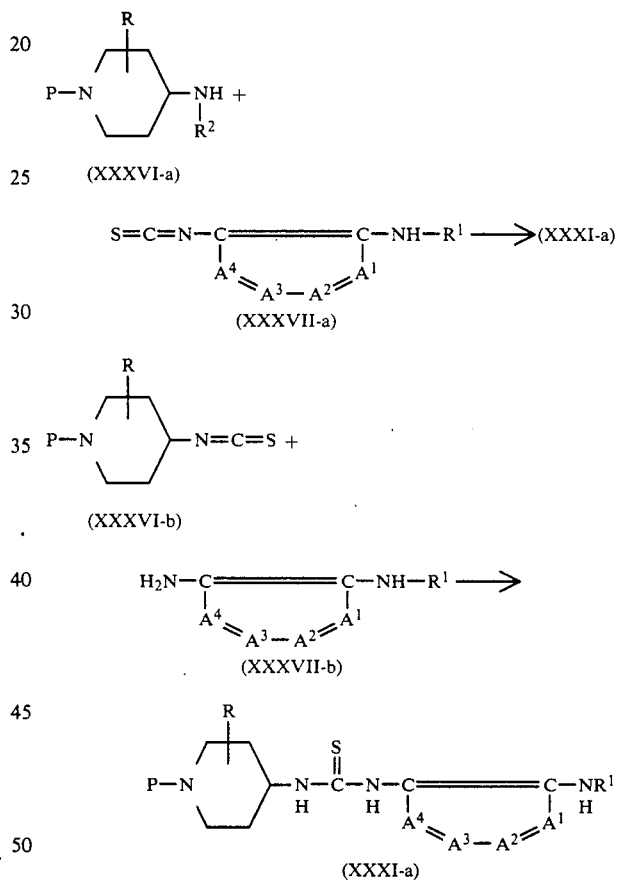

The intermediates of formula (XII) can conveniently be prepared by reacting an intermediate (XV) with a reagent of formula (XXXVIII)

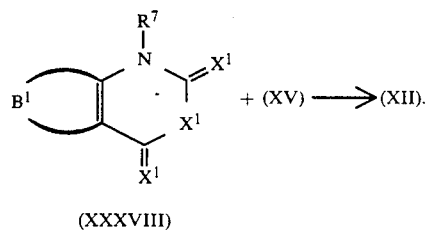

The intermediates of formula (XV) may be prepared by N-alkylating an intermediate (III-a) with a suitable N-protected reagent, followed by an appropriate deprotection reaction.

The intermediates of formula (XIX) may be prepared by N-alkylating (III-a) with a reagent $R^9$—CO—NH—K—W.

The intermediates of formula (XXII) wherein W is halo, said intermediates being represented by the formula (XXII-a), can be prepared by halogenating an intermediate (XXXIX), which can be prepared by N-alkylating (III-a) with a reagent of formula R—CH$_2$—CO—K—W.

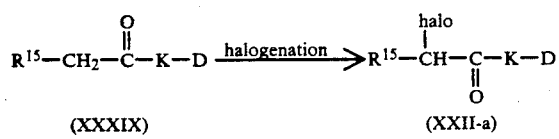

(XXXIX)  (XXII-a)

The intermediates of formula (XXIV) wherein K is —NH—Alk—, said intermediates being represented by the formula (XXIV-a), may be prepared by reacting an intermediate of formula (VI), wherein $X^1$ is S, (VI-a), with ammonia or an ammonium salt, e.g. ammonium chloride, in the presence of a suitable solvent such as, for example, a lower alcohol, e.g. methanol.

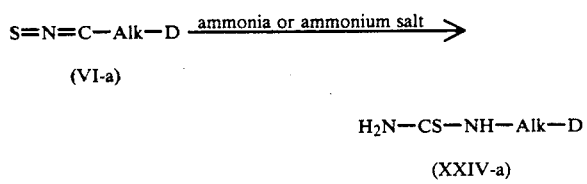

The intermediates of formula (XXV) and (XXVII) may be prepared by reacting an intermediate (III) with an appropriate reagent of formula (XL), respectively (XLI) following the same procedures as described hereinabove for the preparation of (I) starting from (II).

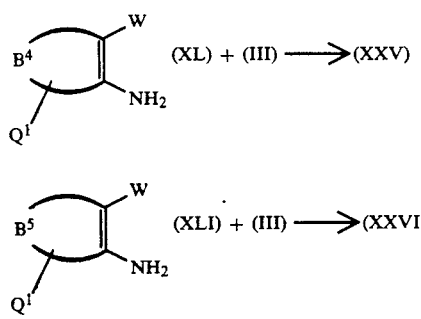

The intermediates of formula (XXVIII) wherein K is —NH—Alk—, said intermediates being represented by the formula (XXVIII-a), may be prepared by reacting an intermediate (VI-a) with a reagent (XLII), optionally in the presence of a suitable solvent.

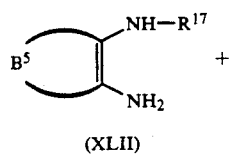

(XLII)

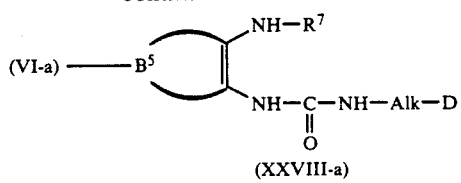

(XXVIII-a)

The intermediates of formula (XXIX) can conveniently be prepared by N-alkylating an intermediate (XLIII). Said intermediate (XLIII) may be prepared by reducing an intermediate (XLIV) following art-known nitro to amine reducing procedures.

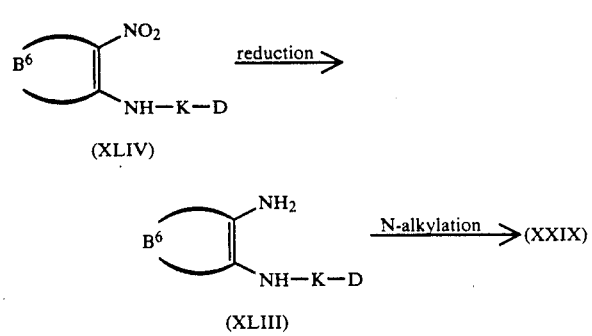

The intermediates of formula (XLIV) may be prepared by alkylating an intermediate of formula (XV) with an appropriate N-alkylating reagent.

The intermediates of formula (XXX) can be prepared by N-acylating an intermediate (III-a) with an appropriate reagent of formula Het—$C_sH_{2s}$—Y—Alk'—CO—$W^2$.

The intermediates of formula (II) can conveniently be prepared following art-known procedures as described in, for example, U.S. Pat. Nos. 4,335,127, 4,342,870 and European Patent Publication No. 0,070,053.

From formula (I) it is evident that the compounds of this invention may have several asymmetric carbon atoms in their structure. Each of these chiral centers may be present in a R- and a S-configuration, this R- and S-notation being in correspondence with the rules described by R. S. Cahn, C. Ingold and V. Prelog in Angew. Chem., Int. Ed. Engl., 5, 385, 511 (1966).

Pure stereochemically isomeric forms of the compounds of formula (I) may be obtained by the application of art-known procedures. Diastereoisomers may be separated by physical separation methods such as selective crystallization and chromatographic techniques, e.g., counter current distribution, and enantiomers may be separated from each other by the selective crystallization of their diastereomeric salts with optically active acids.

Pure stereochemically isomeric forms may also be derived from the corresponding pure stereochemically isomeric forms of the appropriate starting materials, provided that the reaction occurs stereospecifically.

It is evident that the cis and trans diastereomeric racemates may be further resolved into their optical isomers, cis(+), cis(−), trans(+) and trans(−) by the application of methodologies known to those skilled in the art.

Stereochemically isomeric forms of the compounds of formula (I) are naturally intended to be embraced within the scope of the invention.

The following examples are intended to illustrate and not to limit the scope of the present invention. Unless otherwise stated all parts therein are by weight.

EXPERIMENTAL PART

A. Preparation of Intermediates

EXAMPLE 1

A mixture of 90 parts of 4-chloro-3-nitropyridine, 71 parts of 4-fluorobenzenemethanamine, 63 parts of sodium carbonate and 900 parts of N,N-dimethylacetamide was stirred for 1 hour at 50° C. Water was added and the product was extracted with 4-methyl-2-pentanone. The extract was dried, filtered and evaporated. The residue was crystallized from acetonitrile. The product was filtered off and dried, yielding 106 parts (75%) of N-[(4-fluorophenyl)methyl]-3-nitro-4-pyridinamine; mp. 136.8° C. (intermediate 1).

In a similar manner there were also prepared:

$R^{1-a}$—$CH_2$—HN—[ring with $A^1$=$A^2$—$A^3$=$A^4$ and $R''$]

| No. | $R^{1-a}$ | $A^1$=$A^2$—$A^3$=$A^4$ | $R''$ | mp. in °C. |
|---|---|---|---|---|
| 2 | 2-furanyl | CH=CH—CH=CH | $NO_2$ | 85.6 |
| 3 | 4-F—$C_6H_4$ | CH=CH—CH=N | $NH_2$ | — |
| 4 | 4-F—$C_6H_4$ | CH=N(→O)—CH=CH | $NO_2$ | — |
| 5 | 2-pyridinyl | N=CH—CH=CH | $NO_2$ | 113.6 |
| 6 | 2-thienyl | CH=CH—CH=CH | $NO_2$ | — |
| 7 | 4-F—$C_6H_4$ | CH=C($OCH_3$)—CH=CH | $NO_2$ | — |
| 8 | 4-F—$C_6H_4$ | CH=CH—C($OCH_3$)=CH | $NO_2$ | — |
| 9 | 4-F—$C_6H_4$ | CH=CH—C($CH_3$)=CH | $NO_2$ | 99.9 |
| 10 | 2-thienyl | N=CH—CH=CH | $NO_2$ | — |
| 11 | 3-furanyl | N=CH—CH=CH | $NO_2$ | — |
| 12 | 5-methyl-2-furanyl | N=CH—CH=CH | $NO_2$ | — |

EXAMPLE 2

To a stirred and cooled (0° C.) solution of 8.7 parts of N-[(4-fluorophenyl)methyl]-4-nitro-3-pyridinamine, 1-oxide and 150 parts of trichloromethane was added dropwise a solution of 10.2 parts of phosphor trichloride in 75 parts of trichloromethane. Upon completion, the mixture was allowed to reach room temperature and stirring was continued for one hour at reflux temperature. The reaction mixture was cooled and the solvent was evaporated. The residue was stirred in trichloromethane. The product was filtered off and dried, yielding 9 parts of N-[(4-fluorophenyl)methyl]-4-nitro-3-pyridinamine monohydrochloride (intermediate 13).

EXAMPLE 3

A mixture of 56 parts of N-(3-nitro-2-pyridinyl)-2-pyridine-methanamine, 2 parts of a solution of thiophene in ethanone 4% and 400 parts of methanol saturated with ammonia was hydrogenated at normal pressure and at room temperature with 4 parts of platinum-on-charcoal catalyst 5%. After the calculated amount of hydrogen was taken up, the catalyst was filtered off and the filtrate was evaporated. The residue was crystallized from acetonitrile, yielding 43.5 parts of $N^2$-(2-pyridinylmethyl)-2,3-pyridinediamine; mp. 134.9° C. (intermediate 14).

In a similar manner there were also prepared:

$R^{1-a}$—$CH_2$—HN—[ring with $A^1$=$A^2$—$A^3$=$A^4$ and $H_2N$]

| No. | $R^{1-a}$ | $A^1$=$A^2$—$A^3$=$A^4$ | base or salt | mp. in °C. |
|---|---|---|---|---|
| 15 | 2-furanyl | CH=CH—CH=CH | base | — |
| 16 | 4-F—$C_6H_4$ | CH=CH—N=CH | base | 163.7 |
| 17 | 4-F—$C_6H_4$ | CH=N—CH=CH | HCl | 208.9 |
| 18 | 2-thienyl | CH=CH—CH=CH | base | — |
| 19 | 2-furanyl | N=CH—CH=CH | base | — |
| 20 | 4-F—$C_6H_4$ | CH=C($OCH_3$)—CH=CH | base | — |
| 21 | 4-F—$C_6H_4$ | CH=CH—C($OCH_3$)=CH | base | — |
| 22 | 4-F—$C_6H_4$ | CH=CH—C($CH_3$)=CH | base | — |
| 23 | 2-thienyl | N=CH—CH=CH | base | — |
| 24 | 3-furanyl | N=CH—CH=CH | base | — |
| 25 | 5-methyl-2-furanyl | N=CH—CH=CH | base | — |

EXAMPLE 4

To a stirred and cooled mixture of 4 parts of sodium hydroxide in 60 parts of water were added successively 7.9 parts of carbon disulfide and 17.2 parts of ethyl 4-amino-1-piperidinecarboxylate at a temperature below 10° C. Stirring was continued for 30 minutes at this temperature. Then there were added dropwise 10.9 parts of ethyl carbonochloridate (exothermic reaction: temp. rises to about 35° C.). Upon completion, stirring was continued for 2 hours at 60° C. The reaction mixture was cooled and the product was extracted with methylbenzene. The extract was dried, filtered and evaporated, yielding 22 parts (100%) of ethyl 4-isothiocyanato-1-piperidine-carboxylate as a residue (intermediate 26).

EXAMPLE 5

A mixture of 54 parts of ethyl 4-isothiocyanato-1-piperidinecarboxylate, 48 parts of $N^2$-(2-furanylmethyl)-2,3-pyridinediamine and 450 parts of tetrahydrofuran was stirred and refluxed overnight. The reaction mixture was evaporated and the residue was crystallized from a mixture of 2-propanone and 2,2'-oxybispropane. The product was filtered off and dried, yielding 76 parts (75%) of ethyl 4-[[[2-[(2-furanylmethyl)amino]-3-pyridinyl]aminothioxomethyl]amino]-1-piperidinecarboxylate; mp. 132.7° C. (intermediate 27).

In a similar manner there were also prepared:

$CH_3$—$CH_2$—O—C(O)—N[piperidine]N—C(S)—HN—[ring with $R^1$—HN, $A^1$=$A^2$—$A^3$=$A^4$]

base

| No. | $R^1$ | $A^1$=$A^2$—$A^3$=$A^4$ | mp. in °C. |
|---|---|---|---|
| 28 | 2-furanylmethyl | CH=CH—CH=CH | — |
| 29 | 4-F—$C_6H_4$—$CH_2$ | CH=CH—CH=N | — |
| 30 | 4-F—$C_6H_4$—$CH_2$ | CH=CH—N=CH | 166.0 |
| 31 | 4-F—$C_6H_4$—$CH_2$ | CH=N—CH=CH | — |
| 32 | 2-pyridinylmethyl | N=CH—CH=CH | — |
| 33 | H | CH=CF—CF=CH | — |
| 34 | 2-thienylmethyl | CH=CH—CH=CH | — |

-continued

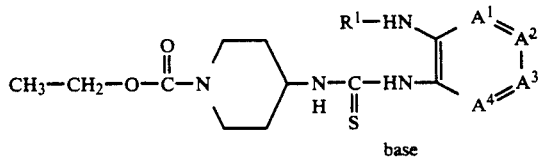

| No. | R¹ | A¹=A²—A³=A⁴ | mp. in °C. |
|---|---|---|---|
| 35 | 4-F—$C_6H_4$—$CH_2$ | CH=CH—C($OCH_3$)=CH | — |
| 36 | 4-F—$C_6H_4$—$CH_2$ | CH=C($OCH_3$)—CH=CH | — |
| 37 | 4-F—$C_6H_4$—$CH_2$ | CH=CH—C($CH_3$)=CH | — |
| 38 | cyclohexyl | CH=CH—CH=CH | — |
| 39 | 2-thienylmethyl | N=CH—CH=CH | — |
| 40 | 3-furanylmethyl | N=CH—CH=CH | — |
| 41 | 5-methyl-2-furanyl-methyl | N=CH—CH=CH | — |

EXAMPLE 6

A mixture of 42.5 parts of ethyl 4-[(phenylmethyl)-amino]-1-piperidinecarboxylate, 30 parts of 1-isothiocyanato-2-nitrobenzene and 270 parts of tetrahydrofuran was stirred for 3 hours at room temperature. 2,2'-Oxybispropane was added and stirring was continued overnight. The precipitated product was filtered off and dried, yielding 48.5 parts (68.5%) of ethyl 4-[[[(2-nitrophenyl)amino)-amino]thioxomethyl](phenylmethyl-)amino]-1-piperidinecarboxylate; mp. 140° C. (intermediate 42).

A mixture of 48.5 parts of ethyl 4-[[[(2-nitrophenyl)-amino)-amino]thioxomethyl](phenylmethyl)amino]-1-piperidinecarboxylate and 600 parts of methanol, saturated with ammonia, was hydrogenated at normal pressure and at 30° C. with 15 parts of palladium-on-charcoal catalyst 10%. After the calculated amount of hydrogen was taken up, the catalyst was filtered off over Hyflo and the filtrate was evaporated, yielding 47 parts (100%) of ethyl 4-[[[(2-aminophenyl)-amino)amino]thioxomethyl](phenylmethyl)amino]-1-piperidinecarboxylate as a residue (intermediate 43).

EXAMPLE 7

A mixture of 74 parts of ethyl 4-[[[2-[(2-furanylmethyl)amino]-3-pyridinyl]aminothioxomethyl]amino]-1-piperidinecarboxylate, 96 parts of mercury(II)oxide, 0.1 parts of sulfur and 800 parts of ethanol was stirred and refluxed for 3 hours. The reaction mixture was filtered over Hyflo and the filtrate was evaporated. The residue was crystallized from acetonitrile, yielding 52.5 parts (79%) of ethyl 4-[[3-(2-furanylmethyl)-3H-imidazo[4,5-b]pyridin-2-yl]amino]-1-piperidinecarboxylate; mp. 149.2° C. (intermediate 44).

In a similar manner there were also prepared:

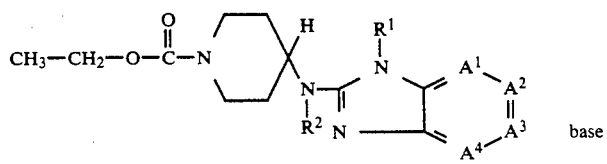

| No. | R¹ | R² | A¹=A²—A³=A⁴ | mp. in °C. |
|---|---|---|---|---|
| 45 | 2-furanylmethyl | H | CH=CH—CH=CH | 135.8 |
| 46 | 4-F—$C_6H_4$—$CH_2$ | H | CH=CH—CH=N | 212.5 |
| 47* | 4-F—$C_6H_4$—$CH_2$ | H | CH=CH—N=CH | — |
| 48* | 4-F—$C_6H_4$—$CH_2$ | H | CH=N—CH=CH | 168.6 |
| 49 | 2-thienylmethyl | H | CH=CH—CH=CH | 142.7 |
| 50 | 2-pyridinylmethyl | H | N=CH—CH=CH | 141.3 |
| 51 | H | H | CH=CF—CF=CH | 234.9 |
| 52 | 4-F—$C_6H_4$—$CH_2$ | H | CH=CH—C($OCH_3$)=CH | — |
| 53 | 4-F—$C_6H_4$—$CH_2$ | H | CH=C($OCH_3$)—CH=CH | — |
| 54 | H | $C_6H_5$—$CH_2$ | CH=CH—CH=CH | — |
| 55 | 4-F—$C_6H_4$—$CH_2$ | H | CH=CH—C($CH_3$)=CH | 202.0 |
| 56 | cyclohexyl | H | CH=CH—CH=CH | — |
| 57 | 2-thienylmethyl | H | N=CH—CH=CH | — |
| 58 | 3-furanylmethyl | H | N=CH—CH=CH | — |
| 59 | 5-methyl-2-furanyl-methyl | H | N=CH—CH=CH | — |

*dihydrochloride monohydrate.

EXAMPLE 8

A mixture of 57.5 parts of ethyl 4-(1H-benzimidazol-2-ylamino)-1-piperidinecarboxylate, 33 parts of 2-(chloromethyl)pyridine hydrochloride, 43 parts of sodium carbonate, 0.1 parts of potassium iodide and 630 parts of N,N-dimethylformamide was stirred and heated overnight at 70° C. The reaction mixture was cooled and poured onto water. The product was extracted with 4-methyl-2-pentanone. The extract was dried, filtered and evaporated. The residue was purified by column chromatography over silica gel using a mixture of trichloromethane and methanol (96:4 by volume) as eluent. The pure fractions were collected and the eluent was evaporated. The residue was crystallized from 4-methyl-2-pentanone, yielding 30 parts (40%) of ethyl 4-[[1-[(2-pyridinyl)methyl]-1H-benzimidazol-2-yl]amino]-1-piperidinecarboxylate; mp. 161.5° C. (intermediate 60).

In a similar manner there were also prepared:

In a similar manner there were also prepared:

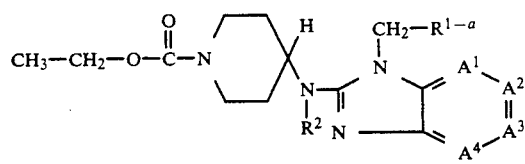

base

| No. | R$^{1-a}$ | R$^2$ | A$^1$=A$^2$—A$^3$=A$^4$ | mp. in °C. |
|---|---|---|---|---|
| 61 | 3-pyridinyl | H | CH=CH—CH=CH | 191.4 |
| 62 | 2-pyrazinyl | H | CH=CH—CH=CH | 178.5-179.3 |
| 63 | 4-F—C$_6$H$_4$ | H | CH=CF—CF=CH | 182.3 |
| 64 | 4-thiazolyl | H | CH=CH—CH=CH | 156.2 |
| 65 | 4-F—C$_6$H$_4$ | CH$_3$ | CH=CH—CH=CH | — |
| 66 | 3-CH$_3$—C$_6$H$_4$ | H | CH=CH—CH=CH | — |
| 67 | 4-F—C$_6$H$_4$ | C$_6$H$_5$—CH$_2$ | CH=CH—CH=CH | — |

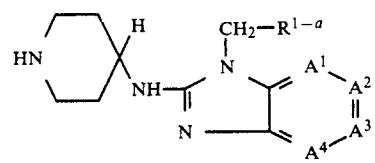

| No. | R$^{1-a}$ | A$^1$=A$^2$—A$^3$=A$^4$ | base or salt form | mp. in °C. |
|---|---|---|---|---|
| 81 | 3-pyridinyl | CH=CH—CH=CH | 3HBr | >260 |
| 82 | 2-pyrazinyl | CH=CH—CH=CH | 3HBr | — |
| 83 | 4-F—C$_6$H$_4$ | CH=CH—CH=N | 2HBr | +300.6 |
| 84 | 4-F—C$_6$H$_4$ | CH=CH—N=CH | 2HBr | 279.4 |
| 85 | 2-pyridinyl | N=CH—CH=CH | 3HBr | 265.5 |
| 86 | 4-F—C$_6$H$_4$ | CH=N—CH=CH | 2HBr.H$_2$O | 291.6 |
| 87 | 4-F—C$_6$H$_4$ | CH=CF—CF=CH | 2HBr | 210.6 |
| 88 | 4-thiazolyl | CH=CH—CH=CH | 2HBr.H$_2$O | 223.5 |
| 89 | 3-CH$_3$C$_6$H$_4$ | CH=CH—CH=CH | 2HBr | — |

EXAMPLE 9

A mixture of 50 parts of ethyl 4-[[3-(2-furanylmethyl)-3H-imidazo[4,5-b]pyridin-2-yl]amino]-1-piperidinecarboxylate, 50 parts of potassium hydroxide, 400 parts of 2-propanol and 20 drops of water was stirred and refluxed for about 5 hours. The reaction mixture was evaporated and water was added to the residue. The product was extracted twice with 4-methyl-2-pentanone. The combined extracts were dried, filtered and evaporated. The solid residue was stirred in 1,1'-oxybisethane. The product was filtered off and dried, yielding 34 parts (85%) of 3-(2-furanylmethyl)-N-(4-piperidinyl)-3H-imidazo[4,5-b]pyridin-2-amine; mp. 159.0° C. (intermediate 68).

In a similar manner there were also prepared:

EXAMPLE 11

50 parts of 1-[(4-fluorophenyl)methyl]-N-(4-piperidinyl)-1H-benzimidazol-2-amine dihydrobromide were taken up in water. The free base was liberated with a sodium hydroxide solution 50% and extracted with dichloromethane. The extract was dried, filtered and evaporated. The residue was boiled in 2-propanone. The product was filtered off and dried, yielding 17 parts (87.5%) of 1-[(4-fluorophenyl)methyl]-N-(4-piperidinyl)-1H-benzimidazol-2-amine; mp. 215.5° C. (intermediate 90).

EXAMPLE 12

A mixture of 2.1 parts of 3-buten-2-one, 9.7 parts of

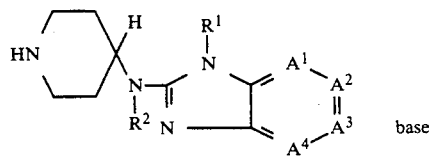

base

| No. | R$^1$ | R$^2$ | A$^1$=A$^2$—A$^3$=A$^4$ | mp. in °C. |
|---|---|---|---|---|
| 69 | 2-furanylmethyl | H | CH=CH—CH=CH | 211.0 |
| 70 | 2-thienylmethyl | H | CH=CH—CH=CH | — |
| 71 | 4-F—C$_6$H$_4$—CH$_2$ | H | CH=CH—C(OCH$_3$)=CH | — |
| 72* | 4-F—C$_6$H$_4$—CH$_2$ | CH$_3$ | CH=CH—CH=CH | 222.2 |
| 73 | 4-F—C$_6$H$_4$—CH$_2$ | H | CH=C(OCH$_3$)—CH=CH | — |
| 74 | 4-F—C$_6$H$_4$—CH$_2$ | H | CH=CH—C(CH$_3$)=CH | — |
| 75 | 4-F—C$_6$H$_4$—CH$_2$ | C$_6$H$_5$—CH$_2$ | CH=CH—CH=CH | — |
| 76 | cyclohexyl | H | CH=CH—CH=CH | 180.0 |
| 77 | 2-thienylmethyl | H | N=CH—CH=CH | — |
| 78 | 3-furanylmethyl | H | N=CH—CH=CH | — |
| 79 | 5-methyl-2-furanyl-methyl | H | N=CH—CH=CH | — |

*dihydrochloride monohydrate.

EXAMPLE 10

A mixture of 30 parts of ethyl 4-[[1-[(2-pyridinyl)methyl]-1H-benzimidazol-2-yl]amino]-1-piperidinecarboxylate and 300 parts of a hydrobromic acid solution 48% in water was stirred and heated for 3 hours at 80° C. The reaction mixture was evaporated and the residue was crystallized from methanol, yielding 41 parts (93.2%) of N-(4-piperidinyl)-1-[(2-pyridinyl)methyl]-1H-benzimidazol-2-amine trihydrobromide; mp. 295.9° C. (intermediate 80).

1-[(4-fluorophenyl)methyl]-N-(4-piperidinyl)-1H-benzimidazol-2-amine and 120 parts of ethanol was stirred for 3 hours at reflux temperature. The reaction mixture was evaporated. The residue was purified by column-chromatography over silica gel using a mixture of trichloromethane and methanol (95:5 by volume) as eluent. The pure fractions were collected and the eluent was evaporated. The residue was crystallized from a mixture of 2-propanone and 2,2'-oxybispropane, yielding 5 parts (42%) of 4-[4-[[1-[(4-fluorophenyl)methyl]-

1H-benzimidazol-2-yl]amino]-1-piperidinyl]-2-butanone; mp. 131.3° C. (intermediate 91).

A stirred solution of 47.5 parts of 4-[4-[[1-[(4-fluorophenyl)-methyl]-1H-benzimidazol-2-yl]amino]-1-piperidinyl]-2-butanone and 500 parts of acetic acid was acidified with a hydrobromic acid solution in glacial acetic acid. Then there were added dropwise 11.8 parts of bromine dissolved in acetic acid. Upon completion, stirring was continued overnight at room temperature. The precipitated product was filtered off and suspended in 2-propanone. The product was filtered off and dried, yielding 23 parts (48.3%) of 1-bromo-4-[4-[[1-[(4-fluorophenyl)methyl]-1H-benzimidazol-2-yl]amino]-1-piperidinyl]-2-butanone dihydrobromide (intermediate 92).

EXAMPLE 13

A mixture of 9 parts of oxirane, 3.24 parts of 1-(4-fluorophenyl-methyl)-N-(4-piperidinyl)-1H-benzimidazol-2-amine and 400 parts of methanol was stirred first overnight at room temperature and further for 4 hours at 50° C. The reaction mixture was evaporated. The residue was purified by column-chromatography over silica gel using a mixture of trichloromethane and methanol, saturated with ammonia, (95:5 by volume) as eluent. The pure fractions were collected and the eluent was evaporated. The residue was crystallized from a mixture of 4-methyl-2-pentanone and 2,2'-oxybispropane, yielding 15 parts of 4-[1-(4-fluorophenylmethyl)-1H-benzimidazol-2ylamino]-1-piperidineethanol; mp. 138.7° C. (intermediate 93).

EXAMPLE 14

A mixture of 11.5 parts of 4-chlorobutanenitrile, 48.5 parts of 1-(4-fluorophenylmethyl)-N-(4-piperidinyl)-1H-benzimidazol-2-amine dihydrobromide, 30 parts of sodium carbonate and 270 parts of N,N-dimethylformamide was stirred and heated overnight at 70° C. The reaction mixture was poured onto water and the product was extracted with trichloromethane. The extract was dried, filtered and evaporated. The residue was crystallized twice from a mixture of 4-methyl-2-pentanone and 2,2'-oxybispropane, yielding 2.2 parts (80%) of 4-[[1-[(4-fluorophenyl)methyl]-1H-benzimidazol-2-yl]-amino]-1-piperidinebutanenitrile; mp. 130.5° C. (intermediate 94).

In a similar manner there were also prepared:

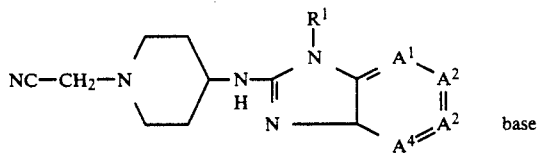

base

| No. | R¹ | —A¹=A²—A³=A⁴— | mp. °C. |
|---|---|---|---|
| 95 | 4-F—C₆H₄—CH₂ | —N=CH—CH=CH— | 183.7 |
| 96 | (2-pyridinyl)methyl | —CH=CH—CH=CH— | 152.6 |
| 97* | 4-F—C₆H₄—CH₂ | —CH=CH—CH=N— | 173.9 |
| 98 | (2-furanyl)methyl | —CH=CH—CH=CH— | 194.4 |
| 99 | (2-pyridinyl)methyl | —N=CH—CH=CH— | 170.0 |
| 100 | (2-furanyl)methyl | —N=CH—CH=CH— | 157.0 |
| 101 | (2-thienyl)methyl | —CH=CH—CH=CH— | 191.7 |
| 102 | C₆H₅—CH₂ | —CH=CH—CH=CH— | 180.4 |
| 103 | 4-F—C₆H₄—CH₂ | —CH=CH—C(OCH₃)=CH | 174.8 |
| 104 | 4-F—C₆H₄—CH₂ | —CH=C(OCH₃)—CH=CH | 222.0 |
| 105 | phenyl | —CH=CH—CH=CH— | — |
| 106 | 3-CH₃C₆H₄—CH₂ | —CH=CH—CH=CH— | — |

*hemihydrate

In a similar manner there was also prepared: 4-[[1-(2-furanylmethyl)-1H-benzimidazol-2-yl]amino]-1-piperidine-butanenitrile (intermediate 107).

EXAMPLE 15

To a stirred mixture of 2.5 parts of lithium aluminum hydride and 225 parts of tetrahydrofuran was added dropwise a solution of 13 parts of 4-[[1-(2-thienylmethyl)-1H-benzimidazol-2-yl]amino]-1-piperidineacetonitrile in tetrahydrofuran under nitrogen atmosphere. Upon completion, stirring was continued for 3 hours at reflux. The reaction mixture was cooled in an ice bath and decomposed by the successive additions of 2.5 parts of water, 7.5 parts of a sodium hydroxide solution 15% and 7.5 parts of water. The whole was filtered over Hyflo and the filtrate was evaporated. The residue was crystallized from acetonitrile, yielding 9.5 parts (72%) of N-[1-(2-aminoethyl)-4-piperidinyl]-1-(2-thienylmethyl)-1H-benzimidazol-2-amine; mp. 137.1° C. (intermediate 108).

EXAMPLE 16

A mixture of 12 parts of 4-[[1-[(4-fluorophenyl)methyl]-1H-imidazo[4,5-b]pyridin-2-yl]amino]-1-piperidineacetonitrile and 200 parts of methanol saturated with ammonia was hydrogenated at normal pressure and at room temperature with 2 parts of Raney-nickel catalyst. After the calculated amount of hydrogen was taken up, the catalyst was filtered off and the filtrate was evaporated. The residue was crystallized from acetonitrile, yielding 10 parts (78%) of N-[1-(2-aminoethyl)-4-piperidinyl]-1-[(4-fluorophenyl)methyl]-1H-imidazo[4,5-b]pyridin-2-amine monohydrate; mp. 116.9° C. (intermediate 109).

Following the same procedure and using equivalent amounts of the appropriate starting materials, there were also prepared:

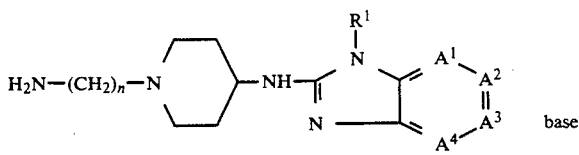

| No. | n | R¹ | —A¹=A²—A³=A⁴— | mp. in °C. |
|---|---|---|---|---|
| 110 | 4 | 4-F—C₆H₄—CH₂ | —CH=CH—CH=CH— | — |
| 111 | 2 | 4-F—C₆H₄—CH₂ | —N=CH—CH=CH— | 174.5 |
| 112 | 2 | (2-pyridinyl)methyl | —CH=CH—CH=CH— | 145.1 |
| 113 | 2 | (2-furanyl)methyl | —CH=CH—CH=CH— | 163.0 |
| 114 | 2 | (2-pyridinyl)methyl | —N=CH—CH=CH— | 151.1 |
| 115* | 2 | (2-furanyl)methyl | —N=CH—CH=CH— | 182.0 |
| 116 | 2 | C₆H₅CH₂ | —CH=CH—CH=CH— | 131.6 |
| 117 | 2 | 4-F—C₆H₄—CH₂ | —CH=CH—C(OCH₃)=CH— | — |
| 118 | 2 | 4-F—C₆H₄—CH₂ | —CH=C(OCH₃)—CH=CH— | — |
| 119 | 2 | C₆H₅ | —CH=CH—CH=CH— | — |
| 120 | 2 | 3-CH₃C₆H₄—CH₂ | —CH=CH—CH=CH— | — |
| 121 | 4 | (2-furanyl)methyl | —CH=CH—CH=CH— | — |

*(E)-2-butenedioate (1:3) monohydrate salt.

EXAMPLE 17

A mixture of 12 parts of N-[1-(2-aminoethyl)-4-piperidinyl]-1-[(4-fluorophenyl)methyl]-5-methoxy-1H-benzimidazol-2-amine and 150 parts of a hydrobromic acid solution 48% in water was stirred and heated for 48 hours at 80° C. The reaction mixture was evaporated and the residue was suspended in 2-propanol. The product was filtered off and dried, yielding 18.5 parts (95.7%) of 2-[[1-(2-aminoethyl)-4-piperidinyl]amino]-1-[(4-fluorophenyl)methyl]-1H-benzimidazol-5-ol trihydrobromide monohydrate mp. +250° C. (intermediate 122).

EXAMPLE 18

To a stirred and cooled (−10° C.) mixture of 12.6 parts of carbon disulfide, 5.2 parts of N,N'-methanetetraylbis[cyclohexanamine] and 45 parts of tetrahydrofuran was added dropwise a solution of 8.5 parts of N-[1-(2-aminoethyl)-4-piperidinyl]-1-(2-furanylmethyl)-1H-benzimidazol-2-amine in 45 parts of tetrahydrofuran. Upon completion, stirring was continued overnight at room temperature. The reaction mixture was evaporated and the residue was purified by column chromatography over silica gel using trichloromethane as eluent. The pure fractions were collected and the eluent was evaporated. The residue was crystallized from acetonitrile, yielding 6.7 parts of 1-(2-furanylmethyl)-N-[1-(2-isothiocyanatoethyl)-4-piperidinyl]-1H-benzimidazol-2-amine (intermediate 123).

In a similar manner there were also prepared:

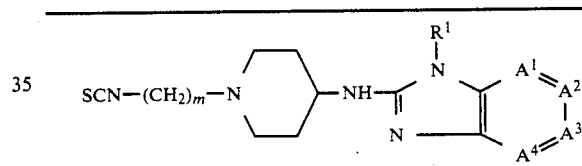

| No. | m | R¹ | —A¹=A²—A³=A⁴— |
|---|---|---|---|
| 124 | 2 | 4-F—C₆H₄—CH₂ | —CH=CH—CH=N— |
| 125 | 2 | (2-pyridinyl)methyl | —N=CH—CH=CH— |
| 126 | 2 | 4-F—C₆H₄—CH₂ | —N=CH—CH=CH— |
| 127 | 2 | (2-pyridinyl)methyl | —CH=CH—CH=CH— |
| 128 | 2 | C₆H₅ | —CH=CH—CH=CH— |
| 129 | 2 | (2-thienyl)methyl | —CH=CH—CH=CH— |
| 130 | 2 | 4-F—C₆H₄—CH₂ | —CH=CH—CH=CH— |
| 131 | 3 | 4-F—C₆H₄—CH₂ | —CH=CH—CH=CH— |
| 132 | 2 | (2-furanyl)methyl | —N=CH—CH=CH— |

EXAMPLE 19

A mixture of 5.4 parts of 3,4-pyridinediamine, 16 parts of 1-(2-furanylmethyl)-N-[1-(2-isothiocyanatoethyl)-4-piperidinyl]-1H-benzimidazol-2-amine and 135 parts of tetrahydrofuran was stirred and refluxed overnight. The reaction mixture was evaporated in vacuo. The residue was purified by column chromatography over silica gel using a mixture of trichloromethane and methanol, saturated with ammonia, (95:5 by volume) as eluent. The pure fractions were collected and the eluent was evaporated, yielding 18 parts (87%) of N-(4-amino-3-pyridinyl)-N'-[2-[4-[[1-(2-furanylmethyl)-1H-benzimidazol-2-yl]amino]-1-piperidinyl]ethyl]thiourea (intermediate 133).

Following the same procedure and using equivalent amounts of the appropriate starting materials, there were also prepared:

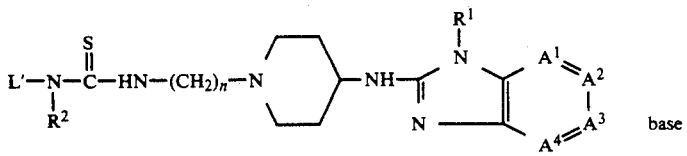

| No. | L' | n | R² | R¹ | —A¹=A²—A³=A⁴— | mp. °C. |
| --- | --- | --- | --- | --- | --- | --- |
| 134 | 4-amino-3-pyridinyl | 2 | H | 4-F—C₆H₄—CH₂ | —CH=CH—CH=CH— | — |
| 135 | 3-amino-2-pyridinyl | 2 | H | 4-F—C₆H₄—CH₂ | —CH=CH—CH=CH— | — |
| 136 | 4-amino-3-pyridinyl | 2 | H | 4-F—C₆H₄—CH₂ | —CH=CH—CH=N— | — |
| 137 | 4-amino-3-pyridinyl | 2 | H | 2-pyridinylmethyl | —N=CH—CH=CH— | — |
| 138 | 4-amino-3-pyridinyl | 2 | H | 4-F—C₆H₄—CH₂ | —N=CH—CH=CH— | — |
| 139 | 4-amino-3-pyridinyl | 2 | H | 2-pyridinylmethyl | —CH=CH—CH=CH— | — |
| 140 | 4-amino-3-pyridinyl | 2 | H | C₆H₅ | —CH=CH—CH=CH— | — |
| 141 | 4-amino-3-pyridinyl | 2 | H | 2-thienylmethyl | —CH=CH—CH=CH— | — |
| 142 | 5-amino-4-pyrimidinyl | 2 | H | 4-F—C₆H₄—CH₂ | —CH=CH—CH=CH— | — |
| 143 | 4-amino-3-pyridinyl | 4 | H | 4-F—C₆H₄—CH₂ | —CH=CH—CH=CH— | — |
| 144 | 4-amino-3-pyridinyl | 3 | H | 4-F—C₆H₄—CH₂ | —CH=CH—CH=CH— | — |
| 145 | 4-amino-3-pyridinyl | 2 | H | 2-furanylmethyl | —N=CH—CH=CH— | — |
| 146 | 4-(methylamino)-3-pyridinyl | 2 | H | 4-F—C₆H₄—CH₂ | —CH=CH—CH=CH— | — |
| 147 | (4-F—C₆H₄CH₂)amino-3-pyridinyl | 2 | H | 4-F—C₆H₄—CH₂ | —CH=CH—CH=CH— | — |
| 148* | 4-amino-3-pyridinyl | 2 | CH₃ | 4-F—C₆H₄—CH₂ | —CH=CH—CH=CH— | 128.1 |

*monohydrate

EXAMPLE 20

A mixture of 120 parts of methanol saturated with ammonia and 4.1 parts of 1-(4-fluorophenylmethyl)-N-[1-(2-isothiocyanatoethyl)-4-piperidinyl]-1H-benzimidazol-2-amine was stirred overnight at room temperature. The reaction mixture was evaporated and the residue was purified by column chromatography over silica gel using a mixture of trichloromethane and methanol (95:5 by volume), saturated with ammonia, as eluent. The pure fractions were collected and the eluent was evaporated. The residue was suspended in 1,1'-oxybisethane. The product was filtered off and crystallized from acetonitrile, yielding 1.1 parts (26%) of N-[2-[4-[[1-[(4-fluorophenyl)methyl]-1H-benzimidazol-2-yl]amino]-1-piperidinyl]ethyl]thiourea; mp. 186.1° C. (intermediate 149).

EXAMPLE 21

A mixture of 3.4 parts of 6-chloro-3-nitro-2-pyridinamine, 7.4 parts of N-[1-(2-aminoethyl)-4-piperidinyl]-1-[(4-fluorophenyl)-methyl]-1H-benzimidazol-2-amine and 10 parts of 1-methyl-2-pyrrolidinone was stirred and heated for 2 hours at 150° C. The reaction mixture was cooled and taken up in methanol saturated with ammonia. The whole was evaporated and water was added to the residue. The product was extracted three times with 4-methyl-2-pentanone. The combined extracts were dried, filtered and evaporated in vacuo. The residue was purified by column chromatography over silica gel using a mixture of trichloromethane and methanol (95:5 by volume) as eluent. The pure fractions were collected and the eluent was evaporated. The residue was crystallized from 4-methyl-2-pentanone, yielding 5 parts (50%) of N⁶-[2-[4-[[1-[(4-fluorophenyl)methyl]-1H-benzimidazol-2-yl]-amino]-1-piperidinyl]ethyl]-3-nitro-2,6-pyridinediamine; mp. 205.7° C. (intermediate 150).

Following the same procedure and using equivalent amounts of the appropriate starting materials, there were also prepared:

1-[(4-fluorophenyl)methyl]-N-[1-[2-[(2-nitrophenyl)amino]ethyl]-4-piperidinyl]-1H-benzimidazol-2-amine; mp. 190.2° C. (intermediate 151); and
6-chloro-N⁴-[2-[4-[[1-[(4-fluorophenyl)methyl]-1H-benzimidazol-2-yl]amino]-1-piperidinyl]ethyl]-4,5-pyrimidinediamine; mp. 216.7° C. (intermediate 152).

EXAMPLE 22

To a stirred mixture of 9.16 parts of 2-amino-5-(methylthio)-benzoic acid and 100 parts of 1,4-dioxane were added dropwise slowly 9.8 parts of trichloromethyl carbonochloridate. Upon completion, stirring was continued for 2 hours. The reaction mixture was evaporated. The residue was crystallized from acetonitrile. The product was filtered off and dried, yielding 8 parts (76%) of 6-(methylthio)-2H-3,1-benzoxazine-2,4(1H)-dione; mp. 219.4° C. (intermediate 153).

EXAMPLE 23

A mixture of 10 parts of N⁶-[2-[4-[[1-[(4-fluorophenyl)-methyl]-1H-benzimidazol-2-yl]amino]-1-piperidinyl]ethyl]-3-nitro-2,6-pyridinediamine, 3 parts of a solution of thiophene in methanol 4% and 400 parts of methanol, saurated with ammonia, was hydrogenated at normal pressure and at room temperature with 4 parts of palladium-on-charcoal catalyst 10%. After the calculated amount of hydrogen was taken up, the catalyst was filtered off and the filtrate was evaporated, yielding 9 parts (94%) of N⁶-[2-[4-[[1-[(4-fluorophenyl)methyl]-1H-benzimidazol-2-yl]amino]-1-piperidinyl]-ethyl]-2,3,6-pyridinetriamine as a residue (intermediate 154).

In a similar manner there was also prepared:
N-[2-[4-[[1-[(4-fluorophenyl)methyl-1H-benzimidazol-2-yl]amino]-1-piperidinyl]ethyl]-1,2-benzenediamine (intermediate 155).

EXAMPLE 24

A mixture of 4.4 parts of N-(5-bromo-1,3,4-thiadiazol-2-yl)-acetamide, 7.3 parts of N-[1-(2-aminoethyl)-4-piperidinyl]-1-[(4-fluorophenyl)methyl]-1H-benzimidazol-2-amine, 3.18 parts of sodium carbonate and 135 parts of N,N-dimethylformamide was stirred overnight at 80°-90° C. The reaction mixture was evaporated. The residue was purified by column chromatography over silica gel using a mixture of trichloromethane and methanol (90:10 by volume) as eluent. The pure fractions were collected and the eluent was evaporated. The residue was crystallized from a mixture of acetonitrile and 2,2'-oxybispropane, yielding 1.7 parts of N-[2-[4-[[1-[(4-fluorophenyl)methyl]-1H-benzimidazol-2-yl]amino]-1-piperidinyl]ethyl]formamide; mp. 153.2° C. (intermediate 156).

EXAMPLE 25

To a stirred and hot (50° C.) mixture of 4.1 parts of 2H-3,1-benzoxazine-2,4(1H)-dione and 31.5 parts of N,N-dimethylformamide was added dropwise a solution of 9.4 parts of N-[1-(2-aminoethyl)-4-piperidinyl]-1-[(4-fluorophenyl)methyl]-1H-benzimidazol-2-amine in 31.5 parts of N,N-dimethylformamide at 50° C. Upon completion, stirring was continued for 3 hours at 50° C. Water was added and the product was extracted with 4-methyl-2-pentanone. The extract was dried, filtered and evaporated. The residue was crystallized from acetonitrile, yielding 9.8 parts (80%) of 2-amino-N-[2-[4-[[1-[(4-fluorophenyl)-methyl]-1H-benzimidazol-2-yl]amino]-1-piperidinyl]-ethyl]benzamide; mp. 171.7° C. (intermediate 157).

In a similar manner there were also prepared:
2-(ethylamino)-N-[2-[4-[[1-[4-(fluorophenyl)methyl]-1H-benzimidazol-2-yl]amino]-1-piperidinyl]ethyl]-benzenamide; mp. 139.8° C. (intermediate 158);
N-[2-[4-[[1-[(4-fluorophenyl)methyl]-1H-benzimidazol-2-yl]amino]-1-piperidinyl]ethyl]-2-(methylamino)-benzamide monohydrate; mp. 147.8° C. (intermediate 159);
2-amino-N-[2-[4-[[1-(2-furanylmethyl)-1H-benzimidazol-2-yl]amino]-1-piperidinyl]ethyl]benzamide; mp. 167.3° C. (intermediate 160);
N-[2-[4-[[1-(2-furanylmethyl)-1H-benzimidazol-2-yl]amino]-1-piperidinyl]ethyl]-2-(methylamino)benzamide monohydrate; mp. 133.0° C. (intermediate 161);
2-amino-N-[4-[4-[[1-(2-furanylmethyl)-1H-benzimidazol-2-yl]amino]-1-piperidinyl]butyl]benzamide; mp. 151.0° C. (intermediate 162);
2-amino-N-[4-[4-[[1-[(4-fluorophenyl)methyl]-1H-benzimidazol-2-yl]-amino]-1-piperidinyl]butyl]benzamide; mp. 186.7° C. (intermediate 163); and
2-amino-N-[2-[4-[[1-[(4-fluorophenyl)methyl]-1H-benzimidazol-2-yl]-amino]-1-piperidinyl]ethyl]-5-(methylthio)benzamide; mp. 184.6° C. (intermediate 164).

EXAMPLE 26

A mixture of 1.5 parts of 6-chloro-N⁴-[2-[4-[[1-[(4-fluorophenyl)methyl]-1H-benzimidazol-2-yl]amino]-1-piperidinyl]ethyl]-4,5-pyrimidinediamine, 3 parts of a solution of thiophene in ethanol 4%, 1 part of potassium acetate and 120 parts of methanol was hydrogenated at normal pressure and at room temperature with 1 part of palladium-on-charcoal catalyst 10%. After the calculated amount of hydrogen was taken up, the catalyst was filtered off and the filtrate was evaporated. The solid residue was taken up in water. The solution was treated with ammonia. The product was extracted with trichloromethane. The organic layer was separated, dried, filtered and evaporated. The residue was crystallized from a mixture of 4-methyl-2-pentanone, yielding 1 part (72.4%) of N⁴-[2-[4-[[1-[(4-fluorophenyl)methyl]-1H-benzimidazol-2-yl]amino]-1-piperidinyl]ethyl]-4,5-pyrimidinediamine; mp. 207.7° C. (intermediate 165).

EXAMPLE 27

A mixture of 30 parts of 4-hydroxy-2-mercapto-6-methyl-5-pyrimidineethanol, 25 parts of potassium carbonate, 270 parts of N,N-dimethylacetamide and 75 parts of water was stirred at room temperature and 36 parts of 1,3-dibromopropane were added at once: temperature rises to 50° C. The whole was stirred overnight at room temperature. The reaction mixture was evaporated and water was added to the residue. The solid product was washed with water and dried in vacuo at 100° C., yielding 21 parts (58%) of 3,4-dihydro-7-(2-hydroxyethyl)-8-methyl-2H,6H-pyrimido[2,1-b][1,3]thiazin-6-one; mp. 155° C. (intermediate 166).

In a similar manner there was also prepared:
2,3-dihyro-6-(2-hydroxyethyl)-7-methyl-5H-thiazolo[3,2-a]pyrimidin-5-one; mp. 148.7° C. (intermediate 167).

EXAMPLE 28

A mixture of 20 parts of 3,4-dihydro-7-(2-hydroxyethyl)-8-methyl-2H,6H-pyrimido[2,1-b][1,3]thiazin-6-one, 50 parts of acetic acid and 180 parts of a hydrobromic acid solution 67% in acetic acid was stirred and heated to reflux. Stirring was continued overnight at reflux temperature. The reaction mixture was evaporated and the solid residue was triturated in 2-propanone. The product was filtered off and dried, yielding 24 parts (100%) of 7-(2-bromoethyl)-3,4-dihydro-8-methyl-2H,6H-pyrimido[2,1-b][1,3]thiazin-6-one monohydrobromide; mp. 215° C. (intermediate 168).

In a similar manner there was also prepared:
6-(2-bromoethyl)-2,3-dihydro-7-methyl-5H-thiazolo[3,2-a]pyrimidin-5-one monohydrobromide; mp. 237.2° C. (intermediate 169).

EXAMPLE 29

A mixture of 27 parts of ethyl 2-[(ethoxycarbonyl)methylamino]benzoate, 16 parts of 2-aminoethanol and 90 parts of dimethylbenzene was stirred and refluxed overnight. The reaction mixture was cooled. The precipitated product was filtered off and crystallized from 2-propanol, yielding 4.5 parts (20%) of 3-(2-hydroxyethyl)-1-methyl-2,4(1H,3H)-quinazolinedione (intermediate 170).

A mixture of 4.5 parts of 3-(2-hydroxyethyl)-1-methyl-2,4(1H,3H)-quinazolinedione, 8 parts of thionyl chloride and 75 parts of trichloromethane was stirred and refluxed for 5 hours. The reaction mixture was evaporated, yielding 4.5 parts (95%) of 3-(2-chloroethyl)-1-methyl-2,4(1H,3H)-quinazolinedione as a residue (intermediate 171).

EXAMPLE 30

A mixture of 50 parts of 2-thiazolamine, 76 parts of 3-acetyl-4,5-dihydro-2(3H)-furanone, 1.2 parts of concentrated hydrochloric acid and 270 parts of methylbenzene was stirred and refluxed for 2 hours using a water-separator. The reaction mixture is cooled and 340 parts of phosphoryl chloride were added at a temperature between 20° and 30° C. The whole was heated slowly to 100°-110° C. and stirring was continued for 2 hours at this temperature. The reaction mixture was evaporated and the residue was poured onto a mixture of crushed ice and ammonium hydroxide. The product was extracted with trichloromethane. The extract was dried, filtered and evaporated. The residue was purified by column chromatography over silica gel using a mixture of trichloromethane and methanol (95:5 by volume) as eluent. The pure fractions were collected and the eluent was evaporated. The residue was crystallized from a mixture of 2-propanol and 1,1'-oxybisethane, yielding 36 parts of 6-(2-chloroethyl)-7-methyl-5H̲-thiazolo[3,2-a]pyrimidin-5-one (intermediate 172).

EXAMPLE 31

A mixture of 4.76 parts of 6-chloro-N⁴-methyl-4,5-pyridinediamine, 26.6 parts of 1,1,1-triethoxyethane and 30 parts of acetic acid anhydride was stirred and refluxed for 3 hours. The reaction mixture was evaporated. The residue was crystallized from a mixture of hexane and methylbenzene. The product was filtered off and dried, yielding 5.3 parts (96.3%) of 6-chloro-8,9-dimethyl-9H̲-purine (intermediate 173).

EXAMPLE 32

A mixture of 4.76 parts of 6-chloro-N⁴methyl-4,5-pyrimidinediamine and 7.2 parts of urea was stirred and heated for 1 hour at 180° C. After cooling, the residue was suspended in water. The product was filtered off and dried, yielding 3.3 parts (60%) of 6-chloro-9-methyl-9H̲-purin-8-ol (intermediate 174).

EXAMPLE 33

A mixture of 9.5 parts of 3-(2-chloroethyl)-2,6-dimethyl-4H̲-pyrido[1,2-a]-pyrimidin-4-one, 160 parts of methanol and 40 parts of 2-propanol saturated with hydrogen chloride was hydrogenated at normal pressure and at room temperature with 2 parts of palladium-on-charcoal catalyst 10%. After the calculated amount of hydrogen was taken up, the catalyst was filtered off over Hyflo and the filtrate was evaporated, yielding 9.5 parts (86%) of 3-(2-chloroethyl)-6,7,8,9-tetrahydro-2,6-dimethyl-4H̲-pyrido[1,2-a]pyrimidin-4-one monohydrochloride (intermediate 175).

In a similar manner there were also prepared:
3-(2-chloroethyl)-6,7,8,9-tetrahydro-2,6,8-trimethyl-4H̲-pyrido[1,2-a]pyrimidin-4-one monohydrochloride (intermediate 176);
3-(2-chloroethyl)-6,7,8,9-tetrahydro-2,7-dimethyl-4H̲-pyrido[1,2-a]pyrimidin-4-one monohydrochloride (intermediate 177).

B. Preparation of Final Compounds

EXAMPLE 34

A mixture of 5.52 parts of 6-(2-bromoethyl)-3,7-dimethyl-5H̲-thiazolo[3,2-a]pyrimidin-5-one monohydrobromide, 7.3 parts of 1-[(4-fluorophenyl)methyl]-N-(4-piperidinyl)-1H̲-benzimidazol-2-amine dihydrobromide, 6.4 parts of sodium carbonate and 135 parts of N,N-dimethylformamide was stirred and heated overnight at 70° C. The reaction mixture was poured onto water. The product was extracted with trichloromethane. The extract was dried, filtered and evaporated. The residue was purified by column chromatography over silica gel using a mixture of trichloromethane and methanol (94:6 by volume), saturated with ammonia, as eluent. The pure fractions were collected and the eluent was evaporated. The residue was crystallized from acetonitrile, yielding 5 parts (62.8%) of 6-[2-[4-[[1-[(4-fluorophenyl)methyl]-1H̲-benzimidazol-2-yl]amino]-1-piperidinyl]ethyl]-3,7-dimethyl-5H̲-thiazolo[3,2-a]pyrimidin-5-one; mp. 141.0° C. (compound 1).

Following the same procedure and using equivalent amounts of the appropriate starting materials, there were also prepared:

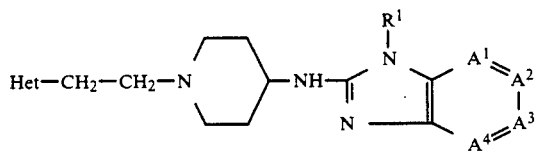

| Comp. No. | Het | R¹ | A¹=A²—A³=A⁴ | base or salt form | m.p. °C. |
|---|---|---|---|---|---|
| 2 | ![benzoxazinone] H-N-C(=O)-N-C(=O) fused benzene | 4-F—C₆H₄—CH₂— | —CH=CH—CH=CH— | H₂O | 222.6 |
| 3 | ![dimethyl pyrimidinedione] O=C-N(CH₃)-...-N-CH=N— with H₃C—N and C=O | 4-F—C₆H₄—CH₂— | —CH=CH—CH=CH— | base | 190.7 |
| 4 | ![methyl pyridopyrimidinone] N, CH₃, N, C=O | 4-F—C₆H₄—CH₂— | —CH=CH—CH=CH— | 3 HCl.2H₂O | 237.3 |

-continued

| Comp. No. | Het | R¹ | A¹=A²—A³=A⁴ | base or salt form | m.p. °C. |
|---|---|---|---|---|---|
| 5 | 2-methyl-4H-pyrido[1,2-a]pyrimidin-4-one-3-yl | 2-furanyl-methyl- | —CH=CH—CH=CH— | base | 108.1 |
| 6 | 2-methyl-4H-pyrido[1,2-a]pyrimidin-4-one-3-yl | 2-furanyl-methyl- | —N=CH—CH=CH— | base | 202.4 |
| 7 | 3,6-dimethyl-7H-thiazolo[3,2-a]pyrimidin-7-one-5-yl | 4-F—C₆H₄—CH₂— | —N=CH—CH=CH— | base | 99.7 |
| 8 | 1,3,7-trimethyl-xanthin-8-yl | 4-F—C₆H₄—CH₂— | —CH=CH—CH=CH— | base | 222.7 |
| 9 | 3,6-dimethyl-7H-thiazolo[3,2-a]pyrimidin-7-one-5-yl | 2-furanyl-methyl- | —CH=CH—CH=CH— | H₂O | 129.1 |
| 10 | 3,6-dimethyl-7H-thiazolo[3,2-a]pyrimidin-7-one-5-yl | 2-furanyl-methyl- | —N=CH—CH=CH— | base | 127.4 |
| 11 | 1,3,7-trimethyl-xanthin-8-yl | 2-furanyl-methyl | —CH=CH—CH=CH— | base | 258.0 |
| 12 | 1,3,7-trimethyl-xanthin-8-yl | 4-F—C₆H₄—CH₂— | —N=CH—CH=CH— | 2 HCl H₂O | 196.1 |

-continued

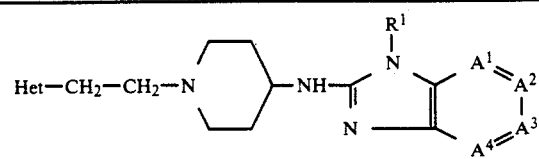

| Comp. No. | Het | R¹ | A¹=A²—A³=A⁴ | base or salt form | m.p. °C. |
|---|---|---|---|---|---|
| 13 | [thiazine-pyrimidinone with S, N, CH₃, N, O] | 2-furanyl-methyl- | —CH=CH—CH=CH— | base | 107.4 |
| 14 | [thiazine-pyrimidinone with S, N, CH₃, N, O] | 2-furanyl-methyl- | —N=CH—CH=CH— | base | 161.2 |
| 15 | [thiazine-pyrimidinone with S, N, CH₃, N, O] | 4-F—C₆H₄—CH₂— | —CH=CH—CH=CH— | 3 HCl 2 H₂O | 229.1 |
| 16 | [thiazine-pyrimidinone with S, N, CH₃, N, O] | 4-F—C₆H₄—CH₂— | —N=CH—CH=CH— | 3 HCl | 239.3 |
| 17 | [thiazine-pyrimidinone with S, N, CH₃, N, O] | 4-F—C₆H₄—CH₂— | —CH=CH—CH=CH— | base | 241.1 |
| 18 | [thiazine-pyrimidinone with S, N, CH₃, N, O] | 2-furanyl-methyl | —CH=CH—CH=CH— | base | 224.5 |
| 19 | [pyrido-pyrimidinone with N, CH₃, N, O] | 4-thiazolyl-methyl | —CH=CH—CH=CH— | base | 167.1 |
| 20 | [pyrido-pyrimidinone with N, CH₃, N, O, CH₃] | 2-furanyl-methyl | —N=CH—CH=CH— | base | 221.0 |
| 21 | [pyrido-pyrimidinone with N, CH₃, N, O, Cl] | 2-furanyl-methyl | —N=CH—CH=CH— | base | 219.7 |

EXAMPLE 35

A mixture of 3.34 parts of 3-(2-chloroethyl)-2-methyl-4H-pyrido-[1,2-a]pyrimidin-4-one, 6 parts of 3-(4-fluorophenylmethyl)-N-(4-piperidinyl)-3H-imidazo[4,5-b]pyridin-2-amine dihydrochloride, 4.8 parts of sodium carbonate, 0.1 parts of potassium iodide and 135 parts of N,N-dimethylformamide was stirred and heated overnight at 70° C. The reaction mixture was poured onto water. The product was extracted with trichloromethane. The extract was dried, filtered and evaporated. The residue was purified by column-chromatography over silica gel using a mixture of trichloromethane and methanol, saturated with ammonia, (96:4 by volume) as eluent. The pure fractions were collected and the eluent was evaporated. The residue was crystallized from acetonitrile, yielding 4 parts (60%) of 3-[2-[4-[[3-[(4-fluorophenyl)methyl]-3H-imidazo[4,5-b]-pyridin-2-yl]amino]-1-piperidinyl]ethyl]-2-methyl-4H-pyrido[1,2-a]pyrimidin-4-one dihydrochloride; mp. 195.7° C. (compound 22).

In a similar manner there were also prepared:

| Comp. No. | L | $R^1$ | $A^1=A^2=A^3=A^4$ | base or salt form | mp. °C. |
|---|---|---|---|---|---|
| 23 | phthalimido-like (N(CH₂)₂ between two C=O on benzene) | 4-F—C₆H₄—CH₂— | —CH=CH—CH=CH— | 2HCl H₂O | 226.9 |
| 24 | benzamide-like with NH—C(=O) and C(=O)—N(CH₂)₂ | 2-furanyl-methyl | —CH=CH—CH=CH— | base | 238.4 |
| 25 | benzamide-like with NH—C(=O) and C(=O)—N(CH₂)₂ | 4-F—C₆H₄—CH₂ | —N=CH—CH=CH— | H₂O | 251.6 |
| 26 | benzamide-like with NH—C(=O) and C(=O)—N(CH₂)₂ | 2-furanyl-methyl | —N=CH—CH=CH— | base | 231.7 |
| 27 | thiazolo-fused ring with CH₃ and (CH₂)₂ C=O | 4-F—C₆H₄—CH₂— | —CH=CH—CH=CH— | base | 115.1 |
| 28 | thiazolo-fused ring with CH₃ and (CH₂)₂ C=O | 2-furanyl-methyl | —N=CH—CH=CH— | base | 186.4 |
| 29 | benzamide-like with NH—C(=O) and C(=O)—N(CH₂)₃ | 4-F—C₆H₄—CH₂— | —CH=CH—CH=CH— | base | 245.3 |

-continued

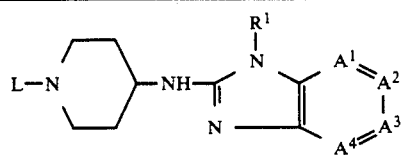

| Comp. No. | L | R¹ | A¹=A²=A³=A⁴ | base or salt form | mp. °C. |
|---|---|---|---|---|---|
| 30 | 2-(NH-CO-CH₂-)-C₆H₄-CO-N(CH₂)₃ | 2-furanyl-methyl | —CH=CH—CH=CH— | base | 250.7 |
| 31 | thiazine-type (S, N, CH₃, (CH₂)₂, C=O, N) | 2-furanyl-methyl | —CH=CH—CH=CH— | base | 103.6 |
| 32 | 2-(NH-CO-CH₂-)-C₆H₄-CO-N(CH₂)₃ | 2-furanyl-methyl | —N=CH—CH=CH— | base | 234.0 |
| 33 | 2-(N(CH₃)-CO-CH₂-)-C₆H₄-CO-N(CH₂)₂ | 4-F—C₆H₄—CH₂— | —CH=CH—CH=CH— | 2HCl H₂O | 207.1 |
| 34 | 2-(N(CH₃)-CO-CH₂-)-C₆H₄-CO-N(CH₂)₂ | 2-furanyl-methyl | —CH=CH—CH=CH— | base | 217.4 |
| 35 | 2-(N(CH₃)-CO-CH₂-)-C₆H₄-CO-N(CH₂)₂ | 2-furanyl-methyl | —N=CH—CH=CH— | base | 195.0 |
| 36 | 2-(N(CH₃)-CO-CH₂-)-C₆H₄-CO-N(CH₂)₂ | 4-F—C₆H₄—CH₂— | —N=CH—CH=CH— | 2HCl | 291.2 |
| 37 | 2-(NH-CO-CH₂-)-C₆H₄-CO-N(CH₂)₃ | 4-F—C₆H₄—CH₂— | —N=CH—CH=CH— | H₂O | 236.1 |

-continued

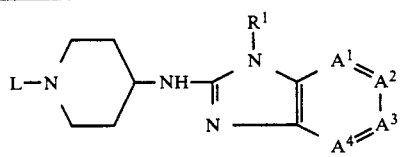

| Comp. No. | L | R¹ | A¹=A²=A³=A⁴ | base or salt form | mp. °C. |
|---|---|---|---|---|---|
| 38 | (thiazine-piperidine fused ring with CH₃, (CH₂)₂) | 4-F—C₆H₄—CH₂— | —N=CH—CH=CH— | 2HCl | 259.6 |
| 39 | (dimethyl-dioxo-pyrimidine-imidazoline fused with (CH₂)₂) | 2-furanyl-methyl | —CH=CH—CH=CH— | base | 192.0 |
| 40 | (pyrimidine-imidazoline fused with CH₃, CH₂) | 4-F—C₆H₄—CH₂— | —CH=CH—CH=CH— | base | 234.8 |
| 41 | (pyridine-imidazoline fused with CH₃, CH₂) | 4-F—C₆H₄—CH₂— | —CH=CH—CH=CH— | base | 196.6 |
| 42 | (dimethyl-dioxo-pyrimidine fused with N(CH₂)₂) | 2-furanyl-methyl | —N=CH—CH=CH— | base | 195.3 |
| 43 | (dimethyl-dioxo-pyrimidine fused with N(CH₂)₂) | 4-F—C₆H₄—CH₂— | —N=CH—CH=CH— | 2HBr H₂O | 246.6 |
| 44 | (pyrido-pyrimidinone with CH₃, (CH₂)₂) | 2-furanyl-methyl | —CH=CH—CH=CH— | 3HCl 3H₂O | 211.2 |
| 45 | (pyrido-pyrimidinone with CH₃, (CH₂)₂) | 4-F—C₆H₄—CH₂— | —CH=CH—CH=CH— | 3HCl 2H₂O | 223.2 |
| 46 | (pyrido-pyrimidinone with CH₃, (CH₂)₂) | 4-F—C₆H₄—CH₂— | —N=CH—CH=CH— | base | 204.8 |

-continued

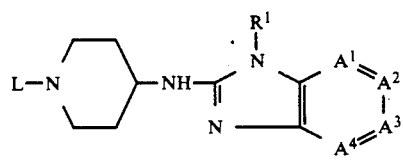

| Comp. No. | L | R¹ | A¹=A²=A³=A⁴ | base or salt form | mp. °C. |
|---|---|---|---|---|---|
| 47 | (tetrahydropyridinyl with (CH₂)₂-C(=O)- and CH₃) | 2-furanyl-methyl | —N=CH—CH=CH— | base | 177.8 |
| 48 | (thiazine ring with S, (CH₂)₂-C(=O)- and CH₃) | 2-furanyl-methyl | —N=CH—CH=CH— | base | 153.8 |
| 49 | (pyrazine fused ring with CH₂ and CH₃) | 4-F—C₆H₄—CH₂— | —CH=CH—CH=CH— | base | 187.1 |
| 50 | (pyridinyl ring with (CH₂)₂-C(=O)- and CH₃) | 4-F—C₆H₄—CH₂— | —CH=CH—C(CH₃)=CH— | base | 168.7 |
| 51 | (pyridinyl ring with (CH₂)₂-C(=O)- and CH₃) | 3-pyridinyl-methyl | —CH=CH—CH=CH— | base | 205.1 |
| 52 | (pyridinyl ring with (CH₂)₂-C(=O)- and CH₃) | 2-thienyl-methyl | —CH=CH—CH=CH— | base | 219.4 |
| 53 | (pyridinyl ring with (CH₂)₂-C(=O)- and CH₃) | 4-F—C₆H₄—CH₂ | —CH=CH—N=CH— | base | 222.3 |
| 54 | (tetrahydropyridinyl ring with (CH₂)₂-C(=O)-, CH₃ and CH₃ substituent) | 2-furanyl-methyl | —N=CH—CH=CH— | base | 175.6 |
| 55 | (pyridinyl ring with (CH₂)₂-C(=O)- and CH₃) | 2-pyridinyl-methyl | —N=CH—CH=CH— | base | 207.3 |

-continued

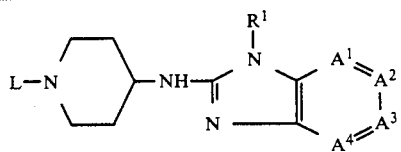

| Comp. No. | L | R[1] | A[1]=A[2]=A[3]=A[4] | base or salt form | mp. °C. |
|---|---|---|---|---|---|
| 56 | 6-methyl-2,3-dihydro-pyrido fused (pyridine with (CH₂)₂ and C=O, CH₃) | 2-pyridinyl-methyl | —CH=CH—CH=CH— | base | 193.3 |
| 57 | piperidine fused with CH₃, (CH₂)₂, C=O | 2-pyridinyl-methyl | —CH=CH—CH=CH— | base | 193.8 |
| 58 | piperidine (CH₃ substituted) fused with CH₃, (CH₂)₂, C=O | 2-furanyl-methyl | —N=CH—CH=CH— | base | 208.4 |
| 59 | piperidine fused with CH₃, (CH₂)₂, C=O | 2-thienyl-methyl | —CH=CH—CH=CH— | base | 214.0 |
| 60 | piperidine fused with CH₃, (CH₂)₂, C=O | 4-F—C₆H₄—CH₂— | —CH=CH—N=CH— | base | 230.5 |
| 61 | piperidine fused with CH₃, (CH₂)₂, C=O | 4-F—C₆H₄—CH₂— | —N=CH—CH=CH— | base | 166.0 |
| 62 | piperidine fused with CH₃, (CH₂)₂, C=O | 4-thiazolyl-methyl | —CH=CH—CH=CH— | base | 158.8 |
| 63 | dimethyl piperidine fused with CH₃, (CH₂)₂, C=O | 2-furanyl methyl | —N=CH—CH=CH— | base | 86.2 |
| 64 | pyrido fused with NH, (CH₂)₂, C=O, C=O | 4-thiazolyl-methyl | —CH=CH—CH=CH— | base | 239.5 |

-continued

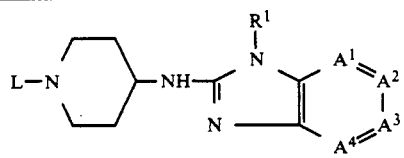

| Comp. No. | L | R¹ | A¹=A²—A³=A⁴ | base or salt form | mp. °C |
|---|---|---|---|---|---|
| 65 | 2-(3-methyl-4-oxo-hexahydropyrido)-pyrimidinyl with (CH₂)₂ | 3-pyridinyl-methyl | —CH=CH—CH=CH— | base | 235.1 |
| 66 | 2-(3H,4H-dioxo-pyrido[1,2-a]pyrimidinyl) with (CH₂)₂ | 2-pyridinyl-methyl | —CH=CH—CH=CH— | base | 238.8 |
| 67 | 2-(3H,4H-dioxo-pyrido[1,2-a]pyrimidinyl) with (CH₂)₂ | 2-pyridinyl-methyl | —N=CH—CH=CH— | base | 240.2 |

EXAMPLE 36

A mixture of 3.15 parts of 3-(2-chloroethyl)-2-methyl-4H-pyrido[1,2-a]pyrimidin-4-one, 8.26 parts of N-(4-piperidinyl)-1-(2-pyrazinylmethyl)-1H-benzimidazol-2-amine trihydrobromide, 6.4 parts of sodium carbonate, 0.1 parts of potassium iodide and 90 parts of N,N-dimethylacetamide was stirred and heated overnight at 80° C. The reaction mixture was poured into water. The product was extracted with trichloromethane. The extract was dried, filtered and evaporated. The residue was purified by column chromatography over silica gel using a mixture of trichloromethane and methanol, saturated with ammonia, (96:4 by volume) as eluent. The pure fractions were collected and the eluent was evaporated. The residue was crystallized from acetonitrile. The product was filtered off and dried, yielding 5 parts (67.4%) of 2-methyl-3-[2-[4-[[1-(2-pyrazinyl-methyl)-1H-benzimidazol-2-yl]amino]-1-piperidinyl]ethyl]-4H-pyrido-[1,2-a]pyrimidin-4-one; mp. 204.4° C. (compound 68).

In a similar manner there were also prepared:

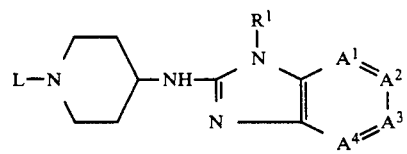

| Comp. No. | L | R¹ | A¹=A²—A³=A⁴ | base or salt form | mp. °C |
|---|---|---|---|---|---|
| 69 | 2-(3-methyl-4-oxo-hexahydropyrido)-pyrimidinyl with (CH₂)₂ | 4-Cl—C₆H₄—CH₂— | —CH=CH—CH=CH— | base | 208.0 |
| 70 | 2-(3-methyl-4-oxo-pyrido)-pyrimidinyl with (CH₂)₂ | 4-F—C₆H₄—CH₂— | —CH=CF—CF=CH— | base | 132.3 |

-continued

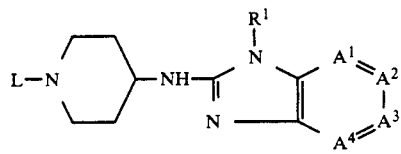

| Comp. No. | L | R¹ | A¹=A²—A³=A⁴ | base or salt form | mp. °C. |
|---|---|---|---|---|---|
| 71 | 2,3,4,5-tetrahydro-6-methyl-pyrido[1,2-a] with (CH₂)₂ and C=O | CH₃—CH₂— | —CH=CH—CH=CH— | 2 HCl ½H₂O | 225.9 |
| 72 | pyrido[1,2-a] CH₃, (CH₂)₂, C=O | H | —CH=CH—CH=CH— | base | 238.5 |
| 73 | pyrido[1,2-a] CH₃, (CH₂)₂, C=O | cyclohexyl | —CH=CH—CH=CH— | base | 156.2 |
| 74 | 7-CH₃ pyrido[1,2-a] CH₃, (CH₂)₂, C=O | 2-furanyl-methyl | —N=CH—CH=CH— | H₂O | 153.3 |
| 75 | 9-CH₃ pyrido[1,2-a] CH₃, (CH₂)₂, C=O | 2-furanyl-methyl | —N=CH—CH=CH— | base | 175.8 |
| 76 | 8-Br pyrido[1,2-a] CH₃, (CH₂)₂, C=O | 2-furanyl-methyl | —N=CH—CH=CH— | H₂O | 218.3 |
| 77 | 7,9-(CH₃)₂ pyrido[1,2-a] CH₃, (CH₂)₂, C=O | 2-furanyl-methyl | —N=CH—CH=CH— | H₂O | 140.6 |
| 78 | 2,3,4,5-tetrahydro pyrido[1,2-a] CH₃, (CH₂)₂, C=O | 4-F—C₆H₄—CH₂— | —CH=CH—C=CH— with CH₃ | base | 192.8 |
| 79 | pyrido[1,2-a] CH₃, (CH₂)₂, C=O | 4-F—C₆H₄—CH₂— | —CH=N—CH=CH— | 3 HCl 2 H₂O | 251.6 |

-continued

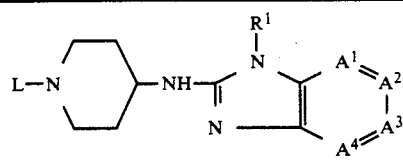

| Comp. No. | L | R¹ | A¹=A²—A³=A⁴ | base or salt form | mp. °C. |
|---|---|---|---|---|---|
| 80 | [pyrido-pyrazine-dione bicyclic with (CH₂)₂] | 2-thienyl-methyl | —CH=CH—CH=CH— | base | 243.4 |
| 81 | [pyrido bicyclic with CH₃ and (CH₂)₂, C=O] | 2-thienyl-methyl | —N=CH—CH=CH— | base | — |
| 82 | [pyrido bicyclic with CH₃ and (CH₂)₂, C=O] | 3-furanyl-methyl | —N=CH—CH=CH— | base | — |
| 83 | [pyrido bicyclic with CH₃ and (CH₂)₂, C=O] | 5-methyl-2-furanyl-methyl | —N=CH—CH=CH— | base | — |
| 84 | [saturated piperidino bicyclic with CH₃ and (CH₂)₂, C=O] | 2-thienyl-methyl | —N=CH—CH=CH— | base | — |
| 85 | [saturated piperidino bicyclic with CH₃ and (CH₂)₂, C=O] | 3-furanyl-methyl | —N=CH—CH=CH— | base | — |
| 86 | [saturated piperidino bicyclic with CH₃ and (CH₂)₂, C=O] | 5-methyl-2-furanyl-methyl | —N=CH—CH=CH— | base | — |
| 87 | [benzo-fused dione with N—(CH₂)₂] | 2-thienyl-methyl | —N=CH—CH=CH— | base | — |
| 88 | [benzo-fused dione with N—(CH₂)₂] | 3-furanyl-methyl | —N=CH—CH=CH— | base | — |

-continued

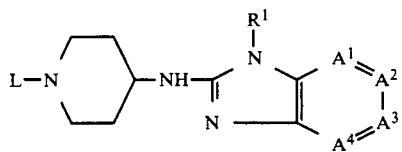

| Comp. No. | L | R¹ | A¹=A²—A³=A⁴ | base or salt form | mp. °C. |
|---|---|---|---|---|---|
| 89 | (2-oxo-2,3-dihydro-1H-quinazolin-3-yl)ethyl via N—(CH₂)₂ | 5-methyl-2-furanyl-methyl | —N=CH—CH=CH— | base | — |

In a similar manner there were also prepared:

3-[2-[4-[[1-[(4-fluorophenyl)methyl]-1H-benzimidazol-2-yl](phenylmethyl)amino]-1-piperidinyl]ethyl]-6,7,8,9-tetrahydro-2-methyl-4H-pyrido[1,2-a]pyrimidin-4-one (E)-2-butenedioate(1:1); mp. 186.4° C. (compound 90);

3-[2-[4-[[1-[(4-fluorophenyl)methyl]-1H-benzimidazol-2-yl]methylamino]-1-piperidinyl]ethyl]-2-methyl-4H-pyrido[1,2-a]pyrimidin-4-one trihydrochloride; mp. 244.7° C. (compound 91); and cis-3-[2-[4-[[1-[(4-fluorophenyl)methyl]-1H-benzimidazol-2-yl]amino]-3-methyl-1-piperidinyl]ethyl]-2-methyl-4H-pyrido[1,2-a]pyrimidin-4-one; mp. 160.6° C. (compound 92).

EXAMPLE 37

A mixture of 2 parts of 6-chloro-9H-purine-9-ethanol, 3.7 parts of N-[1-(2-aminoethyl)-4-piperidinyl]-1-[(4-fluorophenyl)methyl]-1H-benzimidazol-2-amine, 1.06 parts of sodium carbonate and 45 parts of N,N-dimethylacetamide was stirred and heated for 3 hours at 130° C. The reaction mixture was poured into water and the product was extracted with 4-methyl-2-pentanone. The extract was dried, filtered and evaporated. The residue was crystallized from acetonitrile. The product was filtered off and dried, yielding 2.8 parts (53%) of 6-[[2-[4-[[1-[(4-fluorophenyl)methyl]-1H-benzimidazol-2-yl]amino]-1-piperidinyl]ethyl]amino]-9H-purine-9-ethanol; mp. 168.7° C. (compound 93).

In a similar manner there were also prepared:

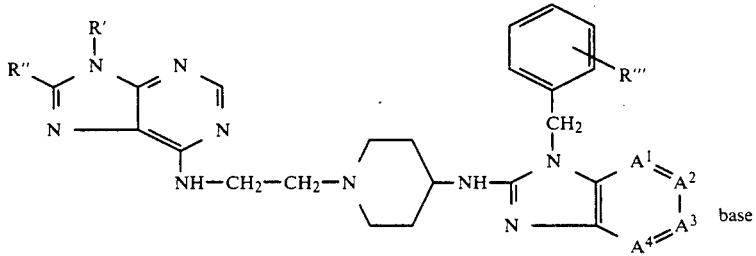

| Comp. | R' | R" | R'" | A¹=A²—A³=A⁴ | mp. °C. |
|---|---|---|---|---|---|
| 94 | CH₃ | H | 4-fluoro | —CH=CH—CH=CH— | 188.0 |
| 95 | C₆H₅CH₂ | H | 4-fluoro | —CH=CH—CH=CH— | 145.5 |
| 96 | CH₃ | CH₃ | 4-fluoro | —CH=CH—CH=CH— | 211.7 |
| 97 | H | H | 4-fluoro | —CH=CH—CH=CH— | 151.4 |
| 98 | CH₃ | OH | 4-fluoro | —CH=CH—CH=CH— | 257.1 |
| 99 | CH₃ | H | 3-CH₃ | —CH=CH—CH=CH— | 188.9 |
| 100 | CH₃ | H | H | —CH=CH—CH=CH— | 207.5 |
| 101 | CH₃ | H | 4-fluoro | —CH=C(OCH₃)—CH=CH— | 194.5 |
| 102 | CH₃ | H | 4-fluoro | —CH=CH—C(OH)=CH— | 186.1 |

EXAMPLE 38

A mixture of 2.8 parts of 2-(methylthio)thiazolo[5,4-b]pyridine and 5.5 parts of N-[1-(2-aminoethyl)-4-piperidinyl]-1-[(4-fluorophenyl)methyl]-1H-benzimidazol-2-amine was stirred for 24 hours at 140° C. The reaction mixture was purified by column chromatography over silica gel using a mixture of trichloromethane and methanol, saturated with ammonia, (97:3 by volume) as eluent. The pure fractions were collected and the eluent was evaporated. The residue was crystallized from acetonitrile. The product was filtered off and dried, yielding 1.9 parts (25%) of N-[2-[4-[[1-[(4-fluorophenyl)-methyl]-1H-benzimidazol-2-yl]amino]-1- piperidinyl]ethyl]thiazolo-[5,4-b]pyridin-2-amine; mp. 203.5° C. (compound 103).

In a similar manner there was also prepared: N-[2-[4-[[1-[(4-fluorophenyl)methyl]-1H-benzimidazol-2-yl]amino]-1-piperidinyl]ethyl]thiazolo[4,5-c]pyridin-2-amine; mp. 192.6° C. (compound 104).

EXAMPLE 39

A mixture of 2.5 parts of thiazolo[5,4-b]pyridine-2-thiol, 1 part of a sodium hydride dispersion 50% and 45 parts of N,N-dimethylformamide was stirred for 1 hour. Then there was added a solution of 6.9 parts of N-[1-(2-chloroethyl)-4-piperidinyl]-1-(4-fluorophenyl-methyl)-1H-benzimidazol-2-amine in 45 parts of N,N-dimethylformamide. The whole was stirred overnight. Water was added dropwise. The product was extracted with 4-methyl-2-pentanone. The extract was dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was crystallized from acetonitrile. The product was filtered off and dried, yielding 0.5 parts (6.4%) of 1-[(4-fluorophenyl)-methyl]-N-[1-[2-(thiazolo[5,4-b]pyridin-2-ylthio)ethyl]-4-piperidinyl]-1H-benzimidazol-2-amine; mp. 159.9° C. (compound 105).

EXAMPLE 40

To a stirred and cooled (0° C.) mixture of 3.8 parts of poly(oxymethylene) 37%, 15.5 parts of 1-[(4-fluorophenyl)methyl]-N-(4-piperidinyl)-1H-benzimidazol-2-amine and 7 parts of glacial acetic acid were added 6.5 parts of 2-methylimidazo[1,2-a]pyridine under nitrogen atmosphere. The whole was heated slowly to 50° C. and stirring was continued at 50° C. for 2 hours. After stirring was continued overnight at room temperature, the reaction mixture was poured into water and the whole was made alkaline with sodium hydroxide. The product was extracted with dichloromethane. The extract was dried, filtered and evaporated. The residue was purified by column chromatography over silica gel using a mixture of trichloromethane and methanol, saturated with ammonia, (96:4 by volume) as eluent. The pure fractions were collected and the eluent was evaporated. The residue was crystallized from acetonitrile. The product was filtered off and dried, yielding 6.7 parts (30%) of 1-[(4-fluorophenyl)methyl]-N-[1-[(2-methylimidazo[1,2-a]pyridin-3-yl)methyl]-4-piperidinyl]-1H-benzimidazol-2-amine; mp. 198.1° C. (compound 106).

EXAMPLE 41

To a stirred mixture of 5.3 parts of 4-[1-(4-fluorophenylmethyl)-1H-benzimidazol-2-ylamino]-1-piperidineethanol dihydrochloride, 2.8 parts of a sodium hydride dispersion 50% and 90 parts of N,N-dimethylformamide were added 2.55 parts of 2-(methylsulfonyl)thiazolo[5,4-b]pyridine. The whole was stirred for 2 hours. The reaction mixture was poured into water. The product was extracted with 4-methyl-2-pentanone. The extract was dried, filtered and evaporated. The residue was purified by column chromatography over silica gel using a mixture of trichloromethane, hexane and methanol (45:45:10 by volume) as eluent. The pure fractions were collected and the eluent was evaporated. The residue was crystallized from acetonitrile. The product was filtered off and dried, yielding 0.9 parts (15%) of 1-[(4-fluorophenyl)methyl]N-[1-[2-[(thiazolo[5,4-b]pyridin-2-yl)oxy]ethyl]-4-piperidinyl]-1H-benzimidazol-2-amine; mp. 151.0° C. (compound 107).

EXAMPLE 42

A mixture of 8 parts of N-[2-[4-[[1-[(4-fluorophenyl)methyl]-1H-benzimidazol-2-yl]amino]-1-piperidinyl]ethyl]-N'-[4-(methylamino)-3-pyridinyl]thiourea, 15 parts of mercury(II)oxide, 0.1 parts of sulfur and 120 parts of ethanol was stirred and refluxed for 3 hours. After the addition of another 15 parts of mercury(II)oxide, stirring at reflux was continued for 2 hours. The reaction mixture was filtered over Hyflo and the filtrate was evaporated. The residue was purified by column chromatography over silica gel using a mixture of trichloromethane and methanol saturated with ammonia (95:5 by volume) as eluent. The pure fractions were collected and the eluent was evaporated. The residue was crystallized from acetonitrile. The product was filtered off and dried, yielding 4.4 parts (59%) of N-[2-[4-[[1-[(4-fluorophenyl)methyl]-1H-benzimidazol-2-yl]amino]-1-piperidinyl]ethyl]-1-methyl-1H-imidazo[4,5-c]pyridin-2-amine monohydrate; mp. 144.6° C. (compound 108).

In a similar manner there were also prepared:

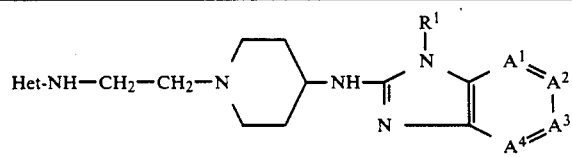

| Comp. No. | Het | R¹ | A¹=A²—A³=A⁴ | base or salt form | mp. °C. |
|---|---|---|---|---|---|
| 109 | ![pyridine-imidazole] | 4-F—C₆H₄—CH₂— | —CH=CH—CH=CH— | base | 250.5 |
| 110 | ![pyridine-imidazole] | 4-F—C₆H₄—CH₂— | —CH=CH—CH=CH— | base | 259.3 |

-continued

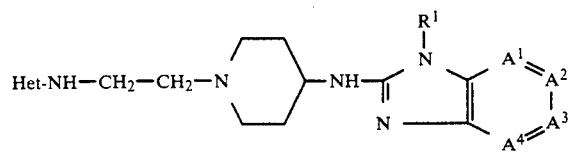

| Comp. No. | Het | R¹ | A¹=A²—A³=A⁴ | base or salt form | mp. °C. |
|---|---|---|---|---|---|
| 111 | imidazo[4,5-c]pyridinyl-NH | 2-furanyl-methyl | —CH=CH—CH=CH— | base | 229.8 |
| 112 | imidazo[4,5-c]pyridinyl-NH | 4-F—C₆H₄—CH₂— | —CH=CH—CH=N— | base | 276.7 |
| 113 | imidazo[4,5-c]pyridinyl-NH | 2-pyridinyl-methyl | —N=CH—CH=CH— | base | 243.0 |
| 114 | imidazo[4,5-c]pyridinyl-NH | 4-F—C₆H₄—CH₂— | —N=CH—CH=CH— | 4(COOH)₂ | 238.8 |
| 115 | imidazo[4,5-c]pyridinyl-NH | 2-pyridinyl-methyl | —CH=CH—CH=CH— | base | 233.0 |
| 116 | imidazo[4,5-c]pyridinyl-NH | phenyl | —CH=CH—CH=CH— | base | 212.6 |
| 117 | imidazo[4,5-c]pyridinyl-NH | 2-thienyl-methyl | —CH=CH—CH=CH— | base | 232.6 |
| 118 | imidazo[4,5-d]pyrimidinyl-NH | 4-F—C₆H₄—CH₂— | —CH=CH—CH=CH— | base | 265.6 |
| 119 | imidazo[4,5-c]pyridinyl-NH | 2-furanyl-methyl | —N=CH—CH=CH— | (E)(CH—COOH)₂ (1:3).H₂O | 169.0 |

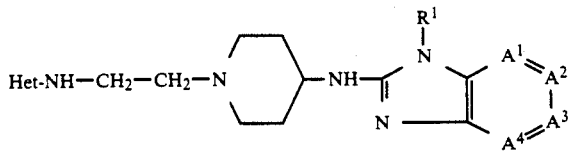

| Comp. No. | Het | R¹ | A¹=A²—A³=A⁴ | base or salt form | mp. °C. |
|---|---|---|---|---|---|
| 120 | (pyridine with CH₂-C₆H₄-F substituent) | 4-F—C₆H₄—CH₂— | —CH=CH—CH=CH— | base | 219.9 |

EXAMPLE 43

A mixture of 18 parts of N-(4-amino-3-pyridinyl)-N'-[4-[4-[[1-[(4-fluorophenyl)methyl]-1H-benzimidazol-2-yl]amino]-1-piperidinyl]-butyl]thiourea, 7 parts of mercury(II)oxide, 1 part of sulfur and 180 parts of tetrahydrofuran was stirred and refluxed for 5 hours. The reaction mixture was filtered hot over Hyflo and the filtrate was evaporated. The residue was purified by column chromatography over silica gel using a mixture of trichloromethane and methanol saturated with ammonia, (90:10 by volume) as eluent. The pure fractions were collected and the eluent was evaporated. The residue was crystallized from a mixture of tetrahydrofuran and trichloromethane, yielding 5 parts (29%) of N-[4-[4-[[1-[(4-fluorophenyl)-methyl]-1H-benzimidazol-2-yl]amino]-1-piperidinyl]butyl]-1H-imidazo-[4,5-c]pyridin-2-amine; mp. 228.2° C. (compound 121).

In a similar manner there were also prepared:
N-[3-[4-[[1-[(4-fluorophenyl)methyl]-1H-benzimidazol-2-yl]amino]-1-piperidinyl]propyl]-1H-imidazo[4,5-c]pyridin-2-amine ethanedioate(2:7); mp. 220.4° C. (compound 122); and
N-[2-[4-[[1-[(4-fluorophenyl)methyl]-1H-benzimidazol-2-yl]amino]-1-piperidinyl]ethyl]-3-methyl-3H-imidazo[4,5-c]pyridin-2-amine ethanedioate(1:3) monohydrate; mp. 242.3° C. (compound 123).

EXAMPLE 44

To a stirred mixture of 7.7 parts of 2-(ethylamino)-N-[2-[4-[[1-[(4-fluorophenyl)methyl]-1H-benzimidazol-2-yl]amino]-1-piperidinyl]-ethyl]benzamide, 2 parts of N,N-diethylethanamine and 90 parts of tetrahydrofuran were added dropwise 1.6 parts of ethyl carbonochloridate. Upon completion, stirring was continued for 1 hour at room temperature. The reaction mixture was evaporated and 4-methyl-2-pentanone was added to the residue. The organic phase was washed with water, dried, filtered and evaporated. The residue was purified by column chromatography over silica gel using a mixture of trichloromethane and methanol (90:10 by volume) as eluent. The pure fractions were collected and the eluent was evaporated. The residue was further purified by HPLC using a mixture of methylbenzene and ethanol (90:10 by volume) as eluent. The pure fraction was collected and the eluent was evaporated. The residue was crystallized from acetonitrile, yielding 2.2 parts (25%) of ethyl [1-[2-[1-ethyl-1,4-dihydro-2,4-dioxo-3(2H)-quinazolinyl]ethyl]-4-piperidinyl]-[1-[(4-fluorophenyl)methyl]-1H-benzimidazol-2-yl]carbamate; mp. 160.3° C. (compound 124).

EXAMPLE 45

To a stirred mixture of 4 parts of 2-(ethylamino)-N-[2-[4-[[1-[(4-fluorophenyl)methyl]-1H-benzimidazol-2-yl]amino]-1-piperidinyl]-ethyl]benzamide, 1.06 parts of sodium carbonate and 65 parts of dichloromethane was added dropwise a solution of 2 parts of methyl carbonochloridate in dichloromethane. Upon completion, stirring was continued overnight at reflux temperature. Water was added and the product was extracted with dichloromethane. The extract was dried, filtered and evaporated. The residue was purified by column chromatography over silica gel using a mixture of trichloromethane and methanol (90:10 by volume) as eluent. The pure fractions were collected and the eluent was evaporated. The residue was converted into the hydrochloride salt in acetonitrile and 2-propanol. The salt was filtered off and dried, yielding 1.8 parts of 1-ethyl-3-[2-[4-[1-[(4-fluorophenyl)methyl]-1H-benzimidazol-2-yl]amino]-1-piperidinyl]ethyl]-2,4(1H,3H)-quinazolinedione dihydrochloride; mp. +260° C. (compound 125).

EXAMPLE 46

A mixture of 6 parts of 2-amino-N-[2-[4-[[1-[(4-fluorophenyl)-methyl]-1H-benzimidazol-2-yl]amino]-1-piperidinyl]ethyl]-5-(methylthio)benzamide, 1.78 parts of 1,1'-carbonylbis[1H-imidazole] and 90 parts of tetrahydrofuran was stirred and refluxed overnight. The reaction mixture was evaporated. The residue was crystallized from acetonitrile. The product was filtered off and dried, yielding 5.2 parts (85%) of 3-[2-[4-[[1-[(4-fluorophenyl)methyl]-1H-benzimidazol-2-yl]amino]-1-piperidinyl]ethyl]-6-(methylthio)-2,4(1H,3H)-quinazolinedione; mp. 238° C. (compound 126).

In a similar manner there were also prepared:
3-[4-[4-[[1-[(4-fluorophenyl)methyl]-1H-benzimidazol-2-yl]amino]-1-piperidinyl]butyl]-2,4(1H,3H)-quinazolinedione; mp. 212.6° C. (compound 127); and
3-[4-[4-[[1-(2-furanylmethyl)-1H-benzimidazol-2-yl]amino]-1-piperidinyl]-butyl]-2,4(1H,3H)-quinazolinedione; mp. 194.3° C. (compound 128).

EXAMPLE 47

To a stirred mixture of 4.7 parts of N-[2-[4-[[1-(2-furanylmethyl)-1H-benzimidazol-2-yl]amino]-1-piperidinyl]ethyl]-2-(methylamino)-benzamide, 2.02 parts of N,N-diethylethanamine and 195 parts of dichloromethane was added dropwise a solution of 1.14 parts of carbonothioic dichloride in dichloromethane. Upon completion, stirring was continued overnight at room temperature. The reaction mixture was poured into water. The layers were separated. The organic layer was dried, filtered and evaporated. The residue was purified by column chromatography over silica gel using a mixture of trichloromethane and methanol, saturated with ammonia, (96:4 by volume) as eluent. The pure fractions were collected and the eluent was evaporated. The residue was crystallized from acetonitrile, yielding 1.4 parts (27.5%) of 3-[2-[4-[[1-(2-furanylmethyl)-1H-benzimidazol-2-yl]amino]-1-piperidinyl]ethyl]-2,3-dihydro-1-methyl-2-thioxo-4(1H)-quinazolinone; mp. 188.4° C. (compound 129).

In a similar manner there was also prepared:
3-[2-[4-[[1-[(4-fluorophenyl)methyl]-1H-benzimidazol-2-yl]amino]-1-piperidinyl]ethyl]-2,3-dihydro-1-methyl-2-thioxo-4(1H)-quinazolinone; mp. 215.8° C. (compound 130).

EXAMPLE 48

To a stirred solution of 10.9 parts of N-[1-(2-aminoethyl)-4-piperidinyl]-1-(4-fluorophenylmethyl)-1H-benzimidazol-2-amine in 150 parts of tetrahydrofuran was added dropwise a solution of 6 parts of methyl 2-isothiocyanatobenzoate in 30 parts of tetrahydrofuran at room temperature: slightly exothermic reaction, the temperature rose to 30° C. Upon completion, stirring at room temperature was continued for one hour. The reaction mixture was evaporated. The residue was stirred in trichloromethane. The formed precipitate was filtered off and crystallized from 2-propanone. The product was filtered off and dried, yielding 5.2 parts of 3-[2-[4-[1-(4-fluorophenylmethyl)-1H-benzimidazol-2-ylamino]-1-piperidinyl]ethyl]-1,2-dihydro-2-thioxo-4(3H)-quinazolinone; mp. 198.5° C. (compound 131).

In a similar manner there were also prepared:
3-[2-[4-[[1-(2-furanylmethyl)-1H-benzimidazol-2-yl]amino]-1-piperidinyl]ethyl]-2,3-dihydro-2-thioxo-4(1H)-quinazolinone; mp. 146.0° C. (compound 132);
3-[2-[4-[[1-[(4-fluorophenyl)methyl]-1H-benzimidazol-2-yl]amino]-1-piperidinyl]ethyl]-2,3-dihydro-6-methyl-2-thioxothieno[2,3-d]pyrimidin-4(1H)-one; mp. 236.4° C. (compound 133); and
3-[2-[4-[[1-(2-furanylmethyl)-1H-benzimidazol-2-yl]amino]-1-piperidinyl]ethyl]-2,3-dihydro-6-methyl-2-thioxothieno[2,3-d]pyrimidin-4(1H)-one monohydrate; mp. 214.5° C. (compound 134).

EXAMPLE 49

To a stirred mixture of 4.1 parts of 3-[2-[4-[[1-[(4-fluorophenyl)methyl]-1H-benzimidazol-2-yl]amino]-1-piperidinyl]ethyl]-2,3-dihydro-6-methyl-2-thioxothieno[2,3-d]pyrimidin-4(1H)-one, 5.6 parts of potassium hydroxide, 81 parts of ethanol and 8 parts of water were added dropwise 60 parts of a hydrogen peroxide solution 3%. The whole was stirred overnight. The reaction mixture was evaporated. The residue was purified by column chromatography over silica gel using a mixture of trichloromethane and methanol (90:10 by volume) as eluent. The pure fractions were collected and the eluent was evaporated. The residue was crystallized from 2-propanone. The product was filtered off and dried, yielding 2.2 parts (55%) of 3-[2-[4-[[1-[(4-fluorophenyl)methyl]-1H-benzimidazol-2-yl]amino]-1-piperidinyl]ethyl]-6-methylthieno[2,3-d]pyrimidine-2,4(1H,3H)-dione; mp. 187.6° C. (compound 135).

In a similar manner there was also prepared:
3-[2-[4-[[1-(2-furanylmethyl)-1H-benzimidazol-2-yl]amino]-1-piperidinyl]ethyl]-6-methylthieno[2,3-d]pyrimidine-2,4(1H,3H)-dione; mp. 151.7° C. (compound 136).

EXAMPLE 50

A mixture of 4.86 parts of 2-amino-N-[2-[4-[[1-[(4-fluorophenyl)-methyl]-1H-benzimidazol-2-yl]amino]-1-piperidinyl]ethyl]benzamide, 1.4 parts of formic acid and 45 parts of methylbenzene was stirred and refluxed overnight. The reaction mixture was evaporated and the residue was taken up in trichloromethane, water and ammonium hydroxide. The organic phase was separated, dried, filtered and evaporated. The residue was crystallized from acetonitrile, yielding 3.6 parts (73%) of 3-[2-[4-[[1-[(4-fluorophenyl)methyl]1H-benzimidazol-2-yl]amino]-1-piperidinyl]ethyl]-4(3H)-quinazolinone; mp. 190.6° C. (compound 137).

EXAMPLE 51

A mixture of 3.7 parts of 2-amino-5-(methylthio)benzoic acid and 8.9 parts of N-[2-[4-[[1-[(4-fluorophenyl)-methyl]-1H-benzimidazol-2-yl]amino]-1-piperidinyl]ethyl]formamide was stirred for 5 hours at 150°-160° C. The whole was purified by column chromatography over silica gel using a mixture of trichloromethane and methanol, saturated with ammonia, (95:5 by volume) as eluent. The pure fractions were collected and the eluent was evaporated. The residue was crystallized from a mixture of 1,1'-oxybisethane and acetonitrile. The product was filtered off and dried, yielding 4.5 parts (41.5%) of 3-[2-[4-[[1-[(4-fluorophenyl)methyl]-1H-benzimidazol-2-yl]amino]-1-piperidinyl]ethyl]-6-(methylthio)-4(3H)-quinazolinone; mp. 101.4° C. (compound 138).

EXAMPLE 52

A mixture of 3 parts of 2-amino-N-[2-[4-[[1-[4-fluorophenyl)-methyl]-1H-benzimidazol-2-yl]amino]-1-piperidinyl]ethyl]benzenamide, 20 parts of acetic acid anhydride and 40 parts of water was stirred overnight at 120° C. The reaction mixture was cooled and ammonium hydroxide was added. The product was extracted with 4-methyl-2-pentanone. The extract was dried, filtered and evaporated. The residue was purified by column chromatography over silica gel using a mixture of trichloromethane and methanol (90:10 by volume) as eluent. The pure fractions were collected and the eluent was evaporated. The residue was crystallized from acetonitrile, yielding 2 parts (67%) of 3-[2-[4-[[1-[(4-fluorophenyl)-methyl]-1H-benzimidazol-2-yl]amino]-1-piperidinyl]ethyl]-2-methyl-4(3H)-quinazolinone; mp. 185.5° C. (compound 139).

In a similar manner there was also prepared:
3-[2-[4-[[1-(2-furanylmethyl)-1H-benzimidazol-2-yl]amino]-1-piperidinyl]ethyl]-2-methyl-4(3H)-quinazolinone; mp. 155.7° C.; (compound 140).

EXAMPLE 53

A mixture of 8.85 parts of 2-amino-N-[2-[4-[[1-[4-fluorophenyl)-methyl]-1H-benzimidazol-2-yl]amino]-1-piperidinyl]ethyl]benzenamide, 1.9 parts of ethyl 2-propynoate and 40 parts of ethanol was stirred and refluxed for 24 hours. The reaction mixture was evaporated. The residue was purified by column chromatography over silica gel using a mixture of trichloromethane and methanol, saturated with ammonia, (95:5 by volume) as eluent. The pure fractions were collected and the eluent was evaporated. The residue was converted into the (E)-2-butenedioate salt in ethanol. The salt was filtered off and dried, yielding 5.1 parts of ethyl 3-[2-[4-[[1-[(4-fluorophenyl)-methyl]-1H-benzimidazol-2-yl]amino]-1-piperidinyl]ethyl]-1,2,3,4-tetrahydro-4-oxo-2-quinazolineacetate (E)-2-butenedioate (1:2); mp. 195.6° C. (compound 141).

EXAMPLE 54

A mixture of 3.2 parts of N-[2-[4-[[1-[(4-fluorophenyl)-methyl]-1H-benzimidazol-2-yl]amino]-1-piperidinyl]ethyl]-1,2-benzenediamine, 1.25 parts of 1,1'-bis[1H-imidazol-1-yl]methanethione and 45 parts of tetrahydrofuran was stirred overnight at room temperature. The reaction mixture was evaporated and the residue was taken up in 4-methyl-2-pentanone. The organic phase was washed twice with water, dried, filtered and evaporated. The residue was purified by column chromatography over silica gel using a mixture of trichloromethane and methanol (90:10 by volume) as eluent. The pure fractions were collected and the eluent was evaporated. The residue was crystallized from acetonitrile, yielding 1.9 parts of 1-[2-[4-[[1-[(4-fluorophenyl)methyl]-1H-benzimidazol-2-yl]amino]-1-piperidinyl]ethyl]-1,3-dihydro-2H-benzimidazole-2-thione; mp. 235.3° C. (compound 142).

EXAMPLE 55

To a stirred mixture of 4.6 parts of $N^4$-[2-[4-[[1-[(4-fluorophenyl)methyl]-1H-benzimidazol-2-yl]amino]-1-piperidinyl]ethyl]-4,5-pyrimidinediamine, 2.25 parts of N,N-diethylethanamine and 195 parts of dichloromethane were added dropwise 1.75 parts of carbonothioic dichloride. Upon completion, stirring was continued for 3 hours at reflux temperature. The reaction mixture was evaporated. The residue was purified by column chromatography over silica gel using a mixture of trichloromethane and methanol, saturated with ammonia, (95:5 by volume) as eluent. The pure fractions were collected and the eluent was evaporated. The residue was converted into the hydrochloride salt in ethanol and 2-propanol. The salt was filtered off and dried, yielding 1 part (15.4%) of 9-[2-[4-[[1-[(4-fluorophenyl)methyl]-1H-benzimidazol-2-yl]amino]-1-piperidinyl]ethyl]-7,9-dihydro-8H-purine-8-thione trihydrochloride dihydrate; mp. 244.7° C. (compound 143).

EXAMPLE 56

7.5 Parts of 6-chloro-$N^4$-[2-[4-[[1-[(4-fluorophenyl)-methyl]-1H-benzimidazol-2-yl]amino]-1-piperidinyl]ethyl]-4,5-pyrimidinediamine and 3.6 parts of urea were heated together till about 220° C. during 10 minutes. The resulting melt was cooled and suspended in water. The solid was filtered off, washed with water and ethanol and recrystallized from a mixture of N,N-dimethylacetamide, ethanol and water, yielding 3.9 parts (49.9%) of 6-chloro-9-[2-[4-[[1-[(4-fluorophenyl)methyl]-1H-benzimidazol-2-yl]amino]-1-piperidinyl]ethyl]-7,9-dihydro-8H-purin-8-one; mp. 266.2° C. (compound 144).

In a similar manner there was also prepared:
9-[2-[4-[[1-[(4-fluorophenyl)methyl]-1H-benzimidazol-2-yl]amino]-1-piperidinyl]ethyl]-7,9-dihydro-8H-purin-8-one; mp. 260.5° C.; (compound 145).

EXAMPLE 57

A mixture of 5 parts of ethyl ethanimidate hydrochloride, 9 parts of $N^6$-[2-[4-[[1-[(4-fluorophenyl)methyl]-1H-benzimidazol-2-yl]-amino]-1-piperidinyl]ethyl]-2,3,6-pyridinetriamine and 100 parts of acetic acid was stirred overnight at room temperature. The reaction mixture was evaporated. The residue was dissolved in trichloromethane. Water was added and sodium hydrogen carbonate was added till foaming had ceased. The layers were separated. The organic layer was dried, filtered and evaporated. The residue was purified by column-chromatography over silica gel using a mixture of trichloromethane and methanol, saturated with ammonia, (95:5 by volume) as eluent. The pure fractions were collected and the eluent was evaporated. The residue was crystallized from 2-propanone. The product was filtered off and dried, yielding 4.8 parts (48.5%) of N-[2-[4-[[1-[(4-fluorophenyl)methyl]-1H-benzimidazol-2-yl]amino]-1-piperidinyl]ethyl]-2-methyl-1H-imidazo[4,5-b]pyridin-5-amine; mp. 202.0° C. (compound 146).

EXAMPLE 58

A mixture of 6.5 parts of ethyl 3-bromo-4-oxo-1-piperidinecarboxylate, 8.6 parts of N-[2-[4-[[1-[(4-fluorophenyl)methyl]-1H-benzimidazol-2-yl]-amino]-1-piperidinyl]ethyl]thiourea and 80 parts of absolute ethanol was stirred and refluxed overnight. The reaction mixture was evaporated and water was added to the residue. The free base was liberated with a sodium hydroxide solution and extracted with 4-methyl-2-pentanone. The extract was dried, filtered and evaporated. The oily residue was converted into the (E)-2-butenedioate salt in 2-propanone and ethanol. The salt was filtered off and dried, yielding 6.66 parts of ethyl 2-[[2-[4-[[1-[4-fluorophenyl)methyl]-1H-benzimidazol-2-yl]amino]-1-piperidinyl]ethyl]-amino]-4,5-dihydro-thiazolo[4,5-d]pyridine-6(7H)-carboxylate (E)-2-butenedioate (1:2) monohydrate; mp. 183.4° C. (compound 147).

EXAMPLE 59

A mixture of 7 parts of 6-chloro-$N^4$-[2-[4-[[1-[(4-fluorophenyl)methyl]-1H-benzimidazol-2-yl]amino]-1-piperidinyl]-ethyl]-4,5-pyrimidinediamine, 2.1 parts of carbon disulfide and 90 parts of N,N-dimethylformamide was stirred overnight at 70° C. The reaction mixture was poured into water. The product was extracted with trichloromethane. The extract was dried, filtered and evaporated. The residue was crystallized from ethanol. The product was filtered off and dried in vacuo overnight at 120° C., yielding 2.3 parts (29%) of 7-[[2-[4-[[1-[(4-fluorophenyl)methyl]-1H-benzimidazol-2-yl]amino]-1-piperidinyl]ethyl]amino]-thiazolo[5,4-d]pyrimidine-2-thiol monohydrochloride; mp. 226.5° C. (compound 148).

EXAMPLE 60

A mixture of 2 parts of 2-thiazolamine, 12.7 parts of 1-bromo-4-[4-[[1-[(4-fluorophenyl)methyl]-1H-benzimidazol-2-yl]amino]-1-piperidinyl]-2-butanone, 6.4 parts of sodium carbonate and 135 parts of methylbenzene was stirred and refluxed for 3 hours using a water separator. The whole was filtered and the filtrate was evaporated. The residue was purified twice by column chromatography over silica gel using a mixture of trichloromethane and methanol, saturated with ammonia, (96:4 by volume) as eluent. The pure fractions were collected and the eluent was evaporated. The residue was crystallized from acetonitrile, yielding 0.5 parts (5.3%) of 1-[(4-fluorophenyl)methyl]-N-[1-[2-(imidazo[2,1-b]thiazol-6-yl)ethyl]-4-piperidinyl]-1H-benzimidazol-2-amine; mp. 222.7° C. (compound 149).

In a similar manner there were also prepared:
1-[(4-fluorophenyl)methyl]-N-[1-[2-(imidazo[1,2-a]pyridin-2-yl)ethyl]-4-piperidinyl]-1H-benzimidazol-2-amine; mp. 208.0° C.; (comp. 150); and
1-[(4-fluorophenyl)methyl]-N-[1-[2-(imidazo[3,2-a]pyrimidin-2-yl)-ethyl]-4-piperidinyl]-1H-benzimidazol-2-amine; mp. 263.8° C.; (compound 151).

EXAMPLE 61

A mixture of 4 parts of 1-[(4-fluorophenyl)methyl]-N-[1-[(imidazo[1,2-a]pyrazin-2-yl)methyl]-4-piperidinyl]-1H-benzimidazol-2-amine, 50 parts of acetic acid and 80 parts of methanol was hydrogenated at normal pressure and at 20° C. with 2 parts of platinum-on-charcoal catalyst 5%. After the calculated amount of hydrogen was taken up, the catalyst was filtered off and the filtrate was evaporated. The residue was purified by column chromatography over silica gel using a mixture of trichloromethane and methanol, saturated with ammonia, (96:4 by volume) as eluent. The pure fractions were collected and the eluent was evaporated. The residue was converted into the hydrochloride salt in ethanol. The salt was filtered off and dried, yielding 1.5 parts (32%) of 1-[(4-fluorophenyl)methyl]-N-[1-[(5,6,7,8-tetrahydroimidazo[1,2-a]pyrazin-2-yl)methyl]-4-piperidinyl]-1H-benzimidazol-2-amine trihydrochloride; mp. 279.7° C. (compound 152).

The useful antihistaminic properties of the compounds of formula (I) are demonstrated in the following test procedure.

Protection of Rats from Compound 48/80-Induced Lethality

Compound 48/80, a mixture of oligomers obtained by condensation of 4-methoxy-N-methylbenzeneethanamine and formaldehyde has been described as a potent histamine releasing agent (Int. Arch. Allergy, 13, 336 (1958)). The protection from compound 48/80-induced lethal circulatory collapse appears to be a simple way of evaluating quantitatively the antihistaminic activity of test compounds. Male rats of an inbred Wistar strain, weighing 240–260 g were used in the experiment. After overnight starvation the rats were transferred to conditioned laboratories (temp. = 21°±1° C., relative humidity = 65±5%).

The rats were treated subcutaneously or orally with a test compound or with the solvent (NaCl solution, 0.9%). One hour after treatment there was injected intravenously compound 48/80, freshly dissolved in water, at a dose of 0.5 mg/kg (0.2 ml/100 g of body weight). In control experiments, wherein 250 solvent-treated animals were injected with the standard dose of compound 48/80, not more than 2.8% of the animals survived after 4 hours. Survival after 4 hours is therefore considered to be a safe criterion of a protective effect of drug administration.

The ED$_{50}$-values of the compounds of formula (I) are listed in the first column of table 1. Said ED$_{50}$-values are the values in mg/kg body weight at which the tested compounds protect 50% of the tested animals against compound 48/80-induced lethality.

The compounds of formula (I) and the pharmaceutically acceptable acid addition salts thereof are also potent serotonin-antagonists. The potency of the subject compounds as serotonin-antagonists is clearly evidenced by the results obtained in the following tests wherein the antagonistic activity of the subject compounds on the effect of serotonin is examined.

ANTAGONISTIC ACTIVITY ON THE EFFECTS OF SEROTONIN IN THE GASTRIC LESION TEST

A. Lesions Induced by Compound 48/80

Compound 48/80 (a mixture of oligomers obtained by condensation of 4-methoxy-N-methylbenzeneethanamine and formaldehyde) is a potent releaser of vasoactive amines from endogenous stores such as, for example, histamine and serotonin. Rats injected with compound 48/80 exhibit consistent changes of blood flow in different vascular beds: cyanosis of the ears and the extremities are prominent within five minutes after injection of the compound; the rats die from shock within 30 minutes. The shock, followed by dead, can be avoided if the rats are pretreated with a classical H 1 antagonist. However the stimulatory effects on gastric secretion are not suppressed so that rats treated with compound 48/80 and protected from shock by an H 1 antagonist may exhibit all signs of intensive gastric gland activity: gross autopsy shows distended stomachs with abnormal contents and rough bright red patches all over the mucosa, corresponding to areas of disintegrated glands. A number of known serotonin-antagonists such as, for example, methysergide, cyproheptadine, cinanserin, mianserin, pipamperone, spiperone, pizotifen and metergoline, prevent completely the cyanosis of ears and extremities as well as the lesions in the glandular area of the stomach and the abnormal gastric distension.

B. Method

Male rats of a Wistar inbred strain, weighing 220–250 g, were starved overnight, water being available ad libitum. The test compounds were administered orally as a solution or as a suspension in aqueous medium. A control rat and a "blank" rat received the test compound. One hour later 5-[4-(diphenylmethyl)-1-piperazinyl-methyl]-1-methyl-1H-benzimidazole-2-methanol was administered subcutaneously to all rats at the dose of 2.5 mg/kg. Two hours after the oral or subcutaneous administration of the test compound, the compound 48/80 (freshly solved in water at a concentration of 0.25 mg/ml) was injected intravenously into all rats (dose: 1 mg/kg) except the "blank" rats. Four hours after the intravenous injection of compound 48/80, the rats were decapitated and the stomachs were removed. Subsequently the stomachs were inspected for distension and contents (blood, fluid, food) and thoroughly rinsed. The macroscopic lesions were scored from 0 to +++, 0 corresponding to complete absence of visible lesions and the highest score corresponding to reddish rough patches covering more than half the glandular area.

The second column of Table 1 shows for a number of compounds of formula (I) the doses (in mg/kg body weight) at which the distension of the stomach as well as the lesions in the glandular area of the stomach are completely absent in 50% of the test rats (ED$_{50}$-value).

The compounds listed in Table 1 are not given for the purpose of limiting the invention thereto but only to exemplify the useful pharmacological activities of all the compounds within the scope of formula (I).

TABLE 1

| Comp. No. | Column 1<br>Compound 48/80<br>lethality test in<br>rats-ED$_{50}$ in mg/kg<br>body weight | Column 2<br>gastric lesion<br>test<br>ED$_{50}$ in mg/kg<br>body weight |
|---|---|---|
| 142 | 0.16 | 0.63 |
| 4 | 0.16 | 0.31 |
| 109 | 0.04 | 0.04 |
| 147 | 0.31 | 0.63 |
| 110 | 0.16 | 0.31 |
| 111 | 0.02 | 0.08 |
| 112 | 0.02 | 0.16 |
| 113 | 0.04 | — |
| 114 | 0.02 | 0.63 |
| 24 | 0.08 | 0.63 |
| 25 | 0.16 | — |
| 5 | 0.16 | 0.04 |
| 22 | 0.16 | — |
| 26 | 0.08 | — |
| 6 | 0.08 | 0.63 |
| 7 | 0.04 | 0.31 |
| 1 | 0.31 | 0.63 |
| 8 | 0.16 | 0.63 |
| 9 | 0.08 | 0.16 |
| 10 | 0.08 | 0.16 |
| 115 | 0.02 | 0.16 |
| 27 | 0.08 | — |
| 11 | 0.08 | 0.04 |
| 12 | 0.16 | 0.31 |
| 28 | 0.04 | 0.16 |
| 30 | 0.16 | — |
| 31 | 0.04 | 0.02 |
| 32 | 0.04 | — |
| 117 | 0.02 | 0.31 |
| 146 | 0.04 | 0.08 |
| 121 | 0.02 | 0.02 |
| 122 | 0.02 | 0.63 |
| 119 | 0.04 | 0.63 |
| 108 | 0.04 | 0.16 |
| 34 | 0.08 | 0.16 |
| 35 | 0.02 | — |
| 13 | 0.02 | 0.08 |
| 14 | 0.02 | — |
| 36 | 0.16 | — |
| 15 | 0.16 | 0.31 |
| 37 | 0.16 | — |
| 16 | 0.16 | — |
| 38 | 0.04 | — |
| 39 | 0.16 | 0.63 |
| 40 | 0.16 | 0.16 |
| 41 | 0.16 | 0.63 |
| 42 | 0.16 | — |
| 43 | 0.16 | — |
| 44 | 0.16 | — |
| 45 | 0.08 | — |
| 132 | 0.16 | — |
| 150 | 0.08 | 0.63 |
| 17 | 0.31 | 0.63 |
| 18 | 0.08 | 0.16 |
| 129 | 0.08 | 0.31 |
| 48 | 0.08 | — |
| 149 | 0.08 | 0.08 |
| 128 | 0.08 | — |
| 151 | 0.08 | — |
| 49 | 0.16 | 0.63 |
| 152 | 0.08 | 0.63 |
| 94 | 0.31 | 0.63 |
| 95 | 0.16 | 0.63 |
| 96 | 0.16 | — |
| 93 | 0.08 | 0.16 |
| 144 | 0.08 | — |
| 97 | 0.08 | 0.04 |
| 143 | 0.31 | 0.63 |
| 107 | 0.16 | — |
| 19 | 0.08 | 0.01 |
| 69 | 0.16 | — |
| 100 | 0.16 | — |
| 103 | 0.16 | 0.63 |
| 70 | 0.31 | 0.63 |
| 102 | 0.08 | — |
| 68 | 0.08 | — |
| 104 | 0.16 | 0.31 |
| 74 | 0.04 | 0.16 |
| 20 | 0.04 | 0.63 |
| 75 | 0.01 | — |
| 76 | 0.08 | — |
| 77 | 0.16 | 0.31 |
| 21 | 0.04 | 0.63 |
| 79 | 0.16 | — |
| 52 | 0.31 | 1.25 |
| 54 | 0.31 | — |
| 55 | 0.08 | 0.16 |
| 57 | 0.16 | — |
| 58 | 0.04 | 0.63 |
| 59 | 0.08 | 0.31 |
| 61 | 0.04 | 0.31 |
| 62 | 0.04 | 0.63 |
| 63 | 0.08 | 0.63 |
| 80 | 0.16 | 0.63 |
| 64 | 0.08 | 0.31 |
| 66 | 0.16 | 0.63 |

In view of their antihistaminic and serotonin-antagonistic properties, the compounds of formula (I) and their acid-addition salts are very useful in the treatment of allergic diseases such as, for example, allergic rhinitis, allergic conjunctivities, chronic urticaria, allergic astma and the like.

In view of their useful pharmacological properties the subject compounds may be formulated into various pharmaceutical forms for administration purposes. To prepare the pharmaceutical compositions of this invention, a pharmaceutically effective amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Acid addition salts of (I), due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The following formulations exemplify typical pharmaceutical compositions in dosage unit form suitable for systemic administration to animal and human subjects in accordance with the present invention. These examples are given to illustrate and not to limit the scope of the present invention.

"Active ingredient" (A.I.) as used throughout these examples relates to a compound of formula (I), a possible stereochemically isomeric form or pharmaceutically acceptable acid addition salt thereof.

EXAMPLE 62

Oral Drops

500 Grams of the A.I. was dissolved in 0.5 liters of 2-hydroxypropanoic acid and 1.5 liters of the polyethylene glycol at 60°–80° C. After cooling to 30°–40° C. there were added 35 liters of polyethylene glycol and the mixture was stirred well. Then there was added a solution of 1750 grams of sodium saccharin in 2.5 liters of purified water and while stirring there were added 2.5 liters of cocoa flavor and polyethylene glycol q.s. to a volume of 50 liters, providing an oral drop solution comprising 10 milligrams of the A.I. per milliliter. The resulting solution was filled into suitable containers.

EXAMPLE 63

Oral Solution

9 Grams of methyl 4-hydroxybenzoate and 1 gram of propyl 4-hydroxybenzoate were dissolved in 4 liters of boiling purified water. In 3 liters of this solution were dissolved first 10 grams of 2,3-dihydroxybutanedioic acid and thereafter 20 grams of the A.I. The latter solution was combined with the remaining part of the former solution and 12 liters 1,2,3-propanetriol and 3 liters of sorbitol 70% solution were added thereto. 40 Grams of sodium saccharin were dissolved in 0.5 liters of water and 2 milliliters of raspberry and 2 milliliters of gooseberry essence were added. The latter solution was combined with the former, water was added q.s. to a volume of 20 liters providing an oral solution comprising 20 milligrams of th active ingredient per teaspoonful (5 milliliters). The resulting solution was filled in suitable containers.

EXAMPLE 64

Capsules

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelating capsules, comprising each 20 milligrams of the active ingredient.

EXAMPLE 65

Film-Coated Tablets

Preparation of tablet core

A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 milliliters of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 milligrams of the active ingredient.

Coating

To a solution of 10 grams methyl cellulose in 75 milliliters of denaturated ethanol there was added a solution of 5 grams of ethyl cellulose in 150 milliliters of dichloromethane. Then there were added 75 milliliters of dichloromethane and 2.5 milliliters 1,2,3-propanetriol. 10 Grams of polyethylene glycol was molten and dissolved in 75 milliliters of dichloromethane. The latter solution was added to the former and then there were added 2.5 grams of magnesium octadecanoate, 5 grams of polyvinylpyrrolidone and 30 milliliters of concentrated colour suspension (Opaspray K-1-2109) and the whole was homogenated.

The tablet cores were coated with the thus obtained mixture in a coating apparatus.

EXAMPLE 66

Injectable Solution 1.8 Grams methyl 4-hydroxybenzoate and 0.2 grams propyl 4-hydroxybenzoate were dissolved in about 0.5 liters of boiling water for injection. After cooling to about 50° C. there were added while stirring 4 grams lactic acid, 0.05 propylene glycol and 4 grams of the A.I.. The solution was cooled to room temperature and supplemented with water for injection q.s. ad 1 liter volume, giving a solution of 4 milligrams A.I. per milliliters. The solution was sterilized by filtration (U.S.P. XVII p. 811) and filled in sterile containers.

EXAMPLE 67

Suppositories

3 Grams A.I. was dissolved in a solution of 3 grams 2,3-dihydroxybutanedioic acid in 25 milliliters polyethylene glycol 400. 12 Grams surfactant and triglycerides q.s. ad 300 grams were molten together. The latter mixture was mixed well with the former solution. The thus obtained mixture was poured onto moulds at a temperature of 37°–38° C. to form 100 suppositories each containing 30 milligrams of the active ingredient.

The present invention is also related with a method of treating allergic diseases in warm-blooded animals suffering from said allergic diseases by administering an effective anti-allergic amount of a compound of formula (I) or a pharmaceutically acceptable acid addition salt thereof.

Suitable doses administered daily to subjects are varying from 0.1 to 100 mg, more preferably from 1 to 50 mg.

What is claimed is:

1. A compound of the formula:

a pharmaceutically acceptable acid addition salt or a possible stereochemically isomeric form thereof, wherein:

$A^1=A^2-A^3=A^4$ represents a bivalent radical of the formula:

—CH=CH—CH=CH— (a);

—N=CH—CH=CH— (b);

—CH=N—CH=CH— (c);

—CH=CH—N=CH— (d); or

—CH=CH—CH=N— (e), wherein one or two hydrogen atoms in said radicals (a)-(e) may, each independently from each other, be replaced by halo, lower alkyl, lower alkyloxy, trifluoromethyl or hydroxy;

R represents a member selected from the group consisting of hydrogen and lower alkyl;

$R^1$ represents a member selected from the group consisting of hydrogen, alkyl, cycloalkyl, $Ar^1$ and lower alkyl substituted with one or two $Ar^1$ radicals, wherein:

$Ar^1$ represents a member selected from the group consisting of phenyl, being optionally substituted with up to three substituents, each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and lower alkyl—CO—; thienyl; halothienyl; furanyl; lower alkyl substituted furanyl; pyridinyl; pyrazinyl; thiazolyl; and imidazolyl optionally substituted by lower alkyl;

$R^2$ represents a member selected from the group consisting of hydrogen, lower alkyl, cycloalkyl, (lower alkyl)—CO—, lower alkyl—O—(CO)— and $Ar^2$-lower alkyl, wherein;

$Ar^2$ represents a member selected from the group consisting of phenyl being optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl, and (lower alkyl)—CO; and L represents a member selected from the group consisting of radicals of the formula:

$Het-C_sH_{2s}-N$ (f)

$Het-C_sH_{2s}-Y-Alk-$; and (g)

$Het-C_sH_{2s}-Z-(C=X)-Y-Alk-$, (h)

wherein:

n represents a number having a value of from 0 to 2;

s represents a number having a value of from 0 to 6;

Alk represents lower alkanediyl;

Y represents O, S, $NR^3$, or a direct bond, wherein $R^3$ represents hydrogen, lower alkyl, ($Ar^2$) lower alkyl, 2-lower alkyloxy-1,2-dioxoethyl or a radical of formula —C(=X)—$R^6$, $R^6$ being hydrogen, lower alkyl, $Ar^2$, $Ar^2$-lower alkyl, lower alkyloxy, $Ar^2$-lower alkyloxy, mono- or di(lower alkyl)amino, $Ar^2$-amino, $Ar^2$-lower alkylamino, or $Ar^2$-lower alkyl(lower alkyl)amino, wherein $Ar^2$ is as defined above;

X represents O, S, CH-$NO_2$, or $NR^4$, wherein $R^4$ represents hydrogen, lower alkyl, cyano, nitro, $Ar^2$-sulfonyl, lower alkylsulfonyl, lower alkylcarbonyl, or $Ar^2$-carbonyl wherein $Ar^2$ is as defined above;

Z represents O, S, $NR^5$, or a direct bond wherein $R^5$ represents hydrogen or lower alkyl; and Het represents a member of the group consisting of a radical of the formula:

wherein:

each $X^1$ independently represents O or S;

$R^7$, $R^8$, and $R^{10}$ are each independently hydrogen, lower alkyl, $Ar^2$-lower alkyl wherein $Ar^2$ is as defined above, hydroxylower alkyl, or lower alkyloxycarbonyl;

$R^9$ and $R^{11}$ are each independently hydrogen, lower alkyl, hydroxy, mercapto, lower alkyloxy, lower alkylthio, halo, and (lower alkyloxycarbonyl)lower alkyl;

$B^1$ represents —CH=CH—CH=CH—, —S—CH=CH—, or —N=CH—NH—;

wherein one or two hydrogen atoms in said radical $B^1$ or in the benzene part of the radicals of formula (i-2) or (i-3) may be replaced by lower alkyl, lower alkylthio, lower alkyloxy, or halo where said hydrogen atom is bonded on a carbon atom, or by lower alkyl, lower alkyloxycarbonyl, Ar$^2$-lower alkyl wherein Ar$^2$ is as defined above, where said hydrogen is bonded on a nitrogen atom, provided that the group R$^7$ or R$^8$, as the case may be, is absent where the radical of formula (i-1) is connected to C$_s$H$_{2s}$ on the nitrogen atom bearing R$^7$ or R$^8$ in the formula, and further provided that (a) when L represents a radical either of formula (f) or of formula (g) wherein Y represents other than a direct bond, or (b) when L represents a radical of formula (h) wherein Z represents other than a direct bond, wherein in said radicals (f), (g), or (h) Het is connected to C$_s$H$_{2s}$ on a nitrogen atom, then s is not 0.

2. A compound according to claim 1 wherein L is a radical of formula (g) or (h).

3. A compound according to claim 1 wherein L is a radical of formula (g).

4. A compound according to claim 3 wherein:
s is 0; and
R$^3$ is hydrogen, lower alkyl, (Ar$^2$) lower alkyl, or —C(=X)—R$^6$ wherein R$^6$ is lower alkyl or lower alkyloxy.

5. A compound according to claim 4 wherein R$^3$ is hydrogen or lower alkyl.

6. A compound according to claim 1 wherein R$^1$ is 4-fluorophenylmethyl, 2-furanylmethyl, 3-furanylmethyl, 4-thiazolylmethyl, 2-pyridinylmethyl, 2-thienylmethyl, or 5-methyl-2-furanylmethyl.

7. An anti-allergic composition comprising suitable pharmaceutical carriers and as active ingredient an anti-allergic effective amount of a compound as defined in claim 1.

8. An anti-allergic composition comprising suitable pharmaceutical carriers and as active ingredient an anti-allergic effective amount of a compound as defined in claim 2.

9. An anti-allergic composition comprising suitable pharmaceutical carriers and as active ingredient an anti-allergic effective amount of a compound as defined in claim 3.

10. An anti-allergic composition comprising suitable pharmaceutical carriers and as active ingredient an anti-allergic effective amount of a compound as defined in claim 4.

11. An anti-allergic composition comprising suitable pharmaceutical carriers and as active ingredient an anti-allergic effective amount of a compound as defined in claim 5.

12. An anti-allergic composition comprising suitable pharmaceutical carriers and as active ingredient an anti-allergic effective amount of a compound as defined in claim 6.

13. A method of treating allergic diseases in warm-blooded animals suffering from same which method comprises the systemic administration to warm-blooded animals of an effective anti-allergic amount of the composition of claim 7.

14. A method of treating allergic diseases in warm-blooded animals suffering from same which method comprises the systemic administration to warm-blooded animals of an effective anti-allergic amount of the composition of claim 8.

15. A method of treating allergic diseases in warm-blooded animals suffering from same which method comprises the systemic administration to warm-blooded animals of an effective anti-allergic amount of the composition of claim 9.

16. A method of treating allergic diseases in warm-blooded animals suffering from same which method comprises the systemic administration to warm-blooded animals of an effective anti-allergic amount of the composition of claim 10.

17. A method of treating allergic diseases in warm-blooded animals suffering from same which method comprises the systemic administration to warm-blooded animals of an effective anti-allergic amount of the composition of claim 11.

18. A method of treating allergic diseases in warm-blooded animals suffering from same which method comprises the systemic administration to warm-blooded animals of an effective anti-allergic amount of the composition of claim 12.

* * * * *